United States Patent
Aymard et al.

(10) Patent No.: US 9,585,402 B2
(45) Date of Patent: Mar. 7, 2017

(54) BISCUIT COMPRISING GUAR GUM

(75) Inventors: Pierre Aymard, Antony (FR); Chantal Simonnot, Campcueil (FR); Gwenaelle Fuzellier, Paris (FR); Agathe Arlotti, Paris (FR)

(73) Assignee: Generale Biscuit, Clamart (FR)

( * ) Notice: Subject to any disclaimer, the term of this patent is extended or adjusted under 35 U.S.C. 154(b) by 487 days.

(21) Appl. No.: 13/125,690

(22) PCT Filed: Oct. 23, 2009

(86) PCT No.: PCT/EP2009/064022
§ 371 (c)(1),
(2), (4) Date: Apr. 22, 2011

(87) PCT Pub. No.: WO2010/046492
PCT Pub. Date: Apr. 29, 2010

(65) Prior Publication Data
US 2011/0229602 A1    Sep. 22, 2011

(30) Foreign Application Priority Data
Oct. 23, 2008 (EP) .................................. 08305721

(51) Int. Cl.
| A21D 10/00 | (2006.01) |
| A21D 2/18 | (2006.01) |
| A21D 13/06 | (2006.01) |

(52) U.S. Cl.
CPC ........... *A21D 2/183* (2013.01); *A21D 13/062* (2013.01); *A23L 7/115* (2016.08); *A23L 29/238* (2016.08); *A23L 33/21* (2016.08); *A23V 2002/00* (2013.01)

(58) Field of Classification Search
USPC ........................................................ 426/549
See application file for complete search history.

(56) References Cited

U.S. PATENT DOCUMENTS 3,543,823 A * 12/1970 Keen .............................. 800/298
4,496,606 A    1/1985 Michnowski
(Continued)

FOREIGN PATENT DOCUMENTS

FR        857128        8/1940
WO    8902225 A1    3/1989
(Continued)

OTHER PUBLICATIONS

Guargum.biz Nov. 8, 2007 http://web.archive.org/web/20071108204704/http://www.guargum.biz/guargum_chemical_structure.html.*
(Continued)

*Primary Examiner* — Katherine D Leblanc
(74) *Attorney, Agent, or Firm* — Fitch, Even, Tabin & Flannery LLP

(57) ABSTRACT

The present invention relates to a biscuit comprising guar gum characterized in that said guar gum is a native guar gum with a length between 0.25 and 8 mm, a width between 0.18 and 2 mm and an average length to width ratio between 1.8 and 6. The invention also relates to the use of said biscuit to help control the blood glucose level in healthy subjects or in subjects suffering from insulino-resistance or diabetes and especially type-2 diabetes and/or to actively lower blood LDL-cholesterol concentration or to maintain normal blood cholesterol concentrations for healthy subjects or subjects at risk of cardiovascular disease. The invention also relates to the use of said biscuit to increase the feelings of satiety, and/or to decrease the food intake and/or to contribute to weight management.

22 Claims, 7 Drawing Sheets

(56) References Cited

U.S. PATENT DOCUMENTS

| | | | |
|---|---|---|---|
| 4,871,557 A | 10/1989 | Linscott | |
| 5,133,984 A | 7/1992 | Murphy | |
| 2002/0094359 A1 | 7/2002 | Prosise | |
| 2002/0192344 A1* | 12/2002 | Brendel et al. | 426/548 |
| 2007/0003686 A1* | 1/2007 | Fichtali et al. | 426/601 |
| 2007/0207248 A1* | 9/2007 | Seneci | 426/573 |

FOREIGN PATENT DOCUMENTS

| | | |
|---|---|---|
| WO | WO 03086083 A1 * | 10/2003 |
| WO | 2007041817 A | 4/2007 |

OTHER PUBLICATIONS

USDA food list Dec. 17, 2012 http://ndb.nal.usda.gov/ndb/foods/show/1?fg=&man=&lfacet=&format=&count=&max=25&offset=&sort=&glookup=.*

USDA Nutritional Database. "Eggs." Retrieved Jun. 29, 2015.*

USDA Nutritional Database. "Whole Milk" Retrieved Jun. 29, 2015.*

USDA Nutrient Database. "Margarine" Retrieved May 9, 2016.*

USDA Nutrient Database. "Rye Flour" Retrieved May 9, 2016.*

USDA Nutrient Database. "Whole Wheat Flour" Retrieved May 9, 2016.*

Apling, E. and Ellis, P. R., "Guar bread: concept to application", Chemistry and Industry (1982), pp. 950-954.

Dea, I. and Morrison, A., "Chemistry and Interactions of Seed Galactomannans", Advances in Carbohydrate Chemistry and Biochemistry (1975), vol. 31, pp. 241-312.

Ellis, P. R., et al., "Evaluation of guar biscuits for use in the management of diabetes: tests of physiological effects and palatability in non-diabetic volunteers.", European Journal of Clinical Nutrition (1988), vol. 42, pp. 425-435.

European Patent Office Search Report for European Application No. 08305721.6, dated Mar. 23, 2009, citing: "Kristin: "How I decided to create granola bars" The Kitchen Sink, [online] Feb. 9, 2008 (Feb. 9, 2008), pp. 1-4, XP002515038 Retrieved from the Internet: http://thekitchensinkrecipes.com/2008/02/09/how-i-decided-to-create-granola-bars/> [retrieved on Feb. 13, 2009]," (8 pages).

Parvathy, K., et al., "Hydration characteristics of guar gum samples and their fractions", Food Hydrocolloids (2007), vol. 21, pp. 630-637.

Kristin: "How I decided to create granola bars" The Kitchen Sink, Retrieved from the Internet: http://thekitchensinkrecipes.com/2008/02/09/how-i-decided-to-create-granola-bars/>, from European Patent Office Search Report for European Application No. 08305721.6, dated Mar. 23, 2009, 23 pages.

* cited by examiner

BISCUIT COMPRISING GUAR GUM

CROSS REFERENCE TO RELATED APPLICATIONS

This application is a national phase application of International Application No. PCT/EP2009/064022, filed Oct. 23, 2009, claiming priority to European Application No. 08305721.6, filed Oct. 23, 2008, both of which are incorporated by reference herein in their entirety.

The present invention relates to a biscuit comprising guar gum in a specific form and the use of said guar in a biscuit to decrease its glycemic and/or insulinemic index.

Since the introduction of the concept of the glycemic index (GI) by Dr. David J. Jenkins and colleagues in their publication entitled "Glycemic index of foods: a physiological basis for carbohydrate exchange" (*Am J Clin Nutr*, 1981, 34 (3), 362-366), there is increasing evidence that diets leading to a reduced glycemic response have favourable impact on diabetes or health markers such as cholesterol ("Low-Glycemic Index diet in the management of diets", Brand Miller et al. 2003, *Diabetes Care;* 26:2261-2267)). Reducing the GI of diet has several health benefits, such as reducing insulin demand, improving blood glucose control and reducing blood lipid concentration. In healthy subjects, suggestive evidence available from epidemiologic studies suggests that a diet based on carbohydrate-rich foods with a low-GI, high-fiber content may reduce the risk of diabetes or cardiovascular disease (Riccardi et al. "Role of Glycemic Index and Glycemic load in the healthy state, in prediabetes, and in diabetes", *Am J Clin Nutr* 2008; 87(1):2695-2745). A possible impact on body weight and satiety has also been suggested in the literature. The benefit of a low GI food is expected only if there is no degradation in global nutritional profile which means a limited fat or saturated fat content in the food.

In this perspective, biscuits having a good nutrition profile (in particular having a low fat and saturated fat content, a low sugar content, and a high fibre content) have been developed lately in order to meet the nutrition requirements regarding food products and to lead to a regular absorption and assimilation of glucose in the blood system when consumed. This steady absorption of glucose is especially beneficial for diabetics and insulin-resistant patients, but is equally interesting for healthy subjects, as part of a healthy diet.

Many studies have shown the interest of fibers, especially viscous soluble fibers, to reduce the glycemic and insulinemic responses. This has been recently summarized by C. L. DIKEMAN and G. C. FAHEY in their article entitled "Viscosity as related to dietary fiber: a review" (*Critical Reviews in Food Science and nutrition*, 2006, 46, 649-663,), which shows the effect of viscous fibers on glycemic and insulinemic response, as well as on blood lipids concentration (cholesterol and triglycerides).

Some well-known food grade texturing agents, used at low dosage (usually from 0.05% to 0.2%) in a variety of food products such as dressings and sauces, dairy products, bakery products, and the like, behave as viscous dietary fibers. Considering their effect on the glycemic and insulinemic response, it became interesting to introduce these viscous dietary fibers, for example guar gum, in dry biscuits to improve their nutritional and functional properties, in particular to obtain products delivering regular glucose during digestion.

However, the incorporation of guar gum in dry biscuits causes important problems on their industrial production, generates a displeasing mouthfeel and brings out a risk of occlusion for the consumer.

Indeed, guar gum is made available as a white to yellowish flour. This flour has a very high affinity for water and tends to bind strongly with the water added during dough mixing. This prevents the formation of a dough suitable for subsequent forming. To correct this situation, it has been tried to increase significantly the hydration of the dough. As a result, the dough becomes unstable, that is to say that its texture and surface properties (stickiness especially) quickly evolve after mixing and make subsequent forming stages difficult. This may require to make a higher number of smaller batches of dough, which is costly and unpractical for the plant.

The increased hydration of the dough also requires to adapt the biscuit baking parameters, for example to increase temperature and/or time of baking, in order to obtain a finished product with the very low moisture content required by the long shelf-life of this category of product.

In addition, in the case of low GI biscuits, the increased dough hydration induces upon baking a modification of the pseudo-crystalline structure of the starch contained in the biscuits into more amorphous or swollen granules. A less crystalline starch becomes more quickly digestible, leading to a rise of glycemic and insulinemic response. This results in the loss of the health benefit of the products developed to provide regular glucose provision and to have low GI.

From an organoleptic point of view, the incorporation of guar flour in the biscuits also modifies the mouth-feel of the biscuit, even at low dosage, such as 2-3% in mass of the final product. Upon mastication, saliva is quickly caught up by the guar gum which hydrates in the mouth and generates a slimy mouthfeel. The biscuit needs to be masticated for a long time and sticks to the teeth, which is displeasing. This may be compensated by increasing either the fat and/or the sugar content, which would restore the melting and lubricate the bolus in the mouth. However, this cannot be done in the case of a nutritional product with low fat and sugar content, for which the incorporation of guar flour dramatically degrades the mouth-feel.

Finally, the introduction of commercial guar flour in dry food products causes safety issues as the swelling process starts immediately after the oral ingestion of the dry material, leading to a high risk of suffocation. For this reason, Public Health Authorities, such as AFSSA in France (2002, n° 2002 SA-0070) consider the use of guar flour not suitable for dry food products, which are intended to rehydrate upon ingestion.

Hence, a challenge in the production of biscuits containing guar gum is to overcome the above mentioned problems regarding the manufacturing process, the mouthfeel, and safety issues to benefit from the guar clinical efficiency.

BRIEF DESCRIPTION OF THE DRAWINGS

For a more complete understanding of the disclosure, reference should be made to the following detailed description and accompanying drawings.

DETAILED DESCRIPTION

Figure 1:
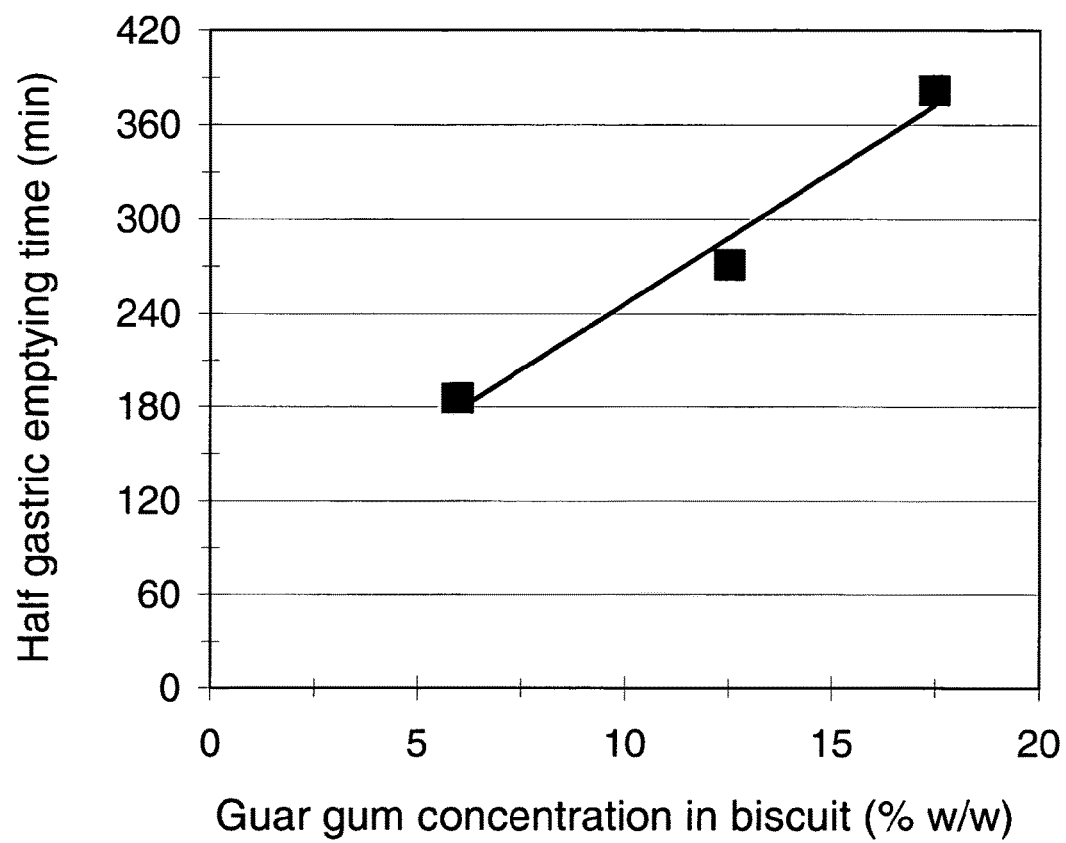
FIG. 1 is a graph showing the gastric half emptying time as a function of guar gum concentration.

It has unexpectedly been found that the above mentioned problems can be avoided by introducing a guar gum having a specific form in dry food products such as biscuits.

Indeed, it has been observed that the use of a specific guar according to the present invention allows the introduction of guar gum in dry food product, without any modification of the biscuit processing, any negative impact on the sensory attributes and any risk of occlusion.

The introduction of the specific guar of the invention in dry food products makes it now possible to obtain biscuits with a good nutritional profile and a low glycemic and/or insulinemic index, while keeping good mouthfeel and sensory properties, and remaining safe for the consumer as regard to occlusion risk.

An object of the present invention is, therefore, a biscuit comprising guar gum characterized in that said guar gum is a native guar gum, with a length between 0.25 and 8 mm, a width between 0.18 and 2 mm and an average length to width ratio between 1.8 and 6.

Another object of the invention is the use of said biscuit having a glycemic index of less or equal than 55, preferably less than 40, more preferably less than 30, even more preferably less than 25, and in a preferred embodiment, less than 20, and/or an insulinemic index of less or equal than or equal 60, preferably less than 40, more preferably less than 30 in the diet of subjects suffering from diabetes and especially type 2 diabetes or insulino-resistance, to help to control the blood glucose level.

A third object of the invention is a process of manufacturing the above-described biscuit comprising the following steps:
(a) Mixing the constituents of the biscuit preferably
  (i) Mixing the powdery components first;
  (ii) Subsequently adding the liquid components;
  (iii) Optionally, adding the larger solid components, such as oat flakes, fruit drops, cereal crisps;
(b) Optionally leaving the dough rest,
(c) Forming the biscuit and oven bake the obtained formed biscuits.

The term "larger solid components" according to the invention are also known as "inclusions" in biscuit technology, and can for example include oat flakes, fruit drops, cereal crisps.

The term "biscuits" is intended to mean a "dry" hard sweet or savoury baked product. In particular, said dry hard sweet or savoury baked product mainly comprises wheat flour and cereals (for example between 20 and 80% of the formula), fats (for example between 2% and 40% of the formula), and/or sugars (for example between 1 and 50% of the formula).

To produce the "biscuits" according to the invention, a first step consists in mixing the ingredients at temperatures between 10° C. and 35° C. in order to obtain a dough, a forming step to give the biscuit its final shape, and a cooking step so as to obtain a biscuit comprising a residual moisture between 0.5% and 5%.

The term "biscuit" according to the invention therefore also includes baked products obtained by such process, for example commercial baked bars known under the brand Nature Valley sold by General Mills or Mini-breaks commercialised by Kellogg's. To sum up, said process comprises the following steps:

Mixing ingredients------->forming a dough------->Baking

However, the term "biscuit" according to the invention does not include the Granola bars such as the Granny® bars commercialized by Lu the one disclosed in document U.S. Pat. No. 4,871,557. Indeed, in the preparation process of Granola bars, a binder comprising water, sugars and fats is prepared and baked, then mixed to the cereals to obtain a dough, formed, and then cooled to obtain the final product. In this process; contrary to the method for preparing biscuits of the invention, the dough composed of the mixed ingredients is not baked. Only the binder is. To sum up, this process comprises the following steps:

Forming a binder and heating------->forming a dough------->Cooling

By "dry product" according to the invention, it should be understood a product having a residual moisture between 0.5% and 5%, preferably between 1% and 4% and more preferably between 1 and 3%, determined by oven desiccation according to NF ISO 712. This low moisture ensures a shelf-life of several months at room temperature.

The term "biscuit matrix" is used to designate the base composed of the constituents of the biscuit.

In a preferred embodiment of the invention, said biscuit comprises less than 25% by weight, relative to the total weight of the biscuit, of sugars, preferably from 2% to 25% by weight of sugar, and/or less than 20% by weight of fat, preferably from 10% to 16% by weight of fat, preferably both.

In a more preferred embodiment, the biscuits according to the present invention are biscuits having a good nutrition profile, that is to say that they comprise:
  a low amount of sugar i.e. below 25%, and preferably below 20%,
  a low amount of fats i.e. below 20%, and preferably below 16%,
  a high amount of cereals i.e. over 30%, and preferably over 40%
  a high amount of fibers i.e. over 6%, and more preferably more than 12% by weight,
these percentages being expressed by weight, relative to the total weight of the biscuit More preferably, the biscuit of the invention can comprise a mixture of three different types of fibers:
  insoluble fibers such as present in whole wheat, oat, barley, rye, rice, and especially in the bran of these cereals, fruits (such apple, citrus, prune, mango, fig, etc), vegetables (such as tomato, carrot, celery, etc) or cocoa.
  soluble fibers that generate a low viscosity in aqueous solution, usually referred to as "non-viscous soluble fibers", such as fructo-oligosaccharides, galacto-oligosaccharides, xylo-oligosaccharides, manno-oligosaccharides, polydextrose, resistant dextrins, cyclo-dextrins, acacia gum, larch gum, and the like.
  viscous soluble fibers, such as guar gum and other galactomannans (locust bean gum, tara gum, fenugreek), glucomannans or konjac flour, psyllium, xanthan, alginates, high-methoxy pectins, beta-glucans from oat or barley, arabinoxylans from wheat, chemically modified cellulosics.

Glycemic Index

The glycemic index (GI) concept was developed at the University of Toronto by Dr. David J. Jenkins and colleagues in their publication entitled "Glycemic index of foods: a physiological basis for carbohydrate exchange." (*Am J Clin Nutr*, 1981, 34 (3), 362-366) in their research to find out which foods were best for people with diabetes. It is a quantitative assessment of foods based on postprandial blood glucose responses, expressed as a percentage of the response to an equivalent carbohydrate portion of a reference food, such as glucose solution. Foods with a low GI can have significant health benefits and are especially suitable for diabetics.

The GI value of a biscuit is measured according to the following method on 12 subjects. This method is fully disclosed in the joint report of the WHO and the FAO, "*Carbohydrates in human nutrition>>*, 1998, accessible online with the following link http://www.fao.org/docrep/W8079E/w8079e00.HTM. Additional specific methodological recommendations were disclosed in the Brouns et al. publication "*Glycaemic index methodology*" Nutrition Research Reviews (2005), 18, 145-171 to ensure the quality of the GI measurement.

Each subject is fed three times with a reference food (glucose solution) and once with the biscuit for which the GI is measured. Each feeding step is separated to another by a period of at least 1 day.

The portion of reference food and tested food both contain 50 grams of available carbohydrates. Available carbohydrates used to be defined by 'total carbohydrates less dietary fibre' (Joint report FAO/WHO), which appears now to be incorrect as it includes non digestible carbohydrates (e.g. fructo-oligosaccharides) that behave from a physiological point of view as fibre. The main potentially sources of available carbohydrates are available starch, maltodextrins, lactose, sucrose, maltose, fructose and glucose, which can be analysed with approved analytical methods (Brouns et al, 2005).

The reference food is prepared by dissolving 51.4 grams of glucose powder (Glucodin® powder, Boots Health Care Company, North Ryde, NSW, Australia) in 250 mL of plain water. The Glucodin® powder contains 97.3 grams of available carbohydrates i.e. glucose per 100 grams of powder.

To calculate the portion of the tested food the contents of total starch, monosaccharides, disaccharides and sugar alcohol by total weight of the biscuit have first to be determined by appropriate analytical procedures. A conversion factor is used to adjust the carbohydrates that are tested to a comparable monosaccahrides equivalent level. 1 g of available starch delivers 1.1 g of glucose units during digestion because of hydration during hydrolysis process. 1 g of available starch delivers 1.05 g of glucose units. A percentage of available carbohydrate relative to the total weight of the biscuit is calculated by the following formula: total starch*1.1+total disaccharides*1.05+total monosaccharides−non-digestible sugars. The portion of the reference food is then calculated to offer a load of 50 gram of available carbohydrate.

Usually, the first day, the subject will be fed with the reference food, and blood glucose level is measured. After at least one day, the subject will be fed again with the reference food and blood glucose level will be measured again. Another break of at least one day is observed. Then the subject is fed with the biscuit for which the GI is measured, and blood glucose level is measured. A standard amount 250 mL of plain water is supplied to the subject with the portion of tested biscuits. After at least a one-day break, the subject will be fed again with the reference food and blood glucose level will be measured again.

It is possible to compare the GI of several tested foods. In this case, the method can be as follow:

The first day, the subject will be fed with the reference food, and blood glucose level is measured. After at least a one-day break, the subject is fed with the biscuit for which the GI is measured (for example a test biscuit comprising no guar), and blood glucose level is measured. Then, the subject will be fed again with the reference food and blood glucose level will be measured again. Another one-day break is observed. Then the subject is fed with the biscuit (for example according to the invention), and blood glucose level is measured. After a two-day break, the subject will be fed again with the reference food and blood glucose level will be measured again.

The blood glucose level is measured each time during 2 hours after consumption. The GI is the Area Under Curve (AUC) of blood glucose after consumption of the tested food divided by the AUC of blood glucose after ingestion of the reference food and multiplied by 100.

A GI is considered low below or equal to 55. In a preferred embodiment, the biscuit has a glycemic index of less than 55, preferably less than 40, more preferably less than 30, even more preferably less than 25, and in a preferred embodiment, less than 20.

In particular, the biscuit of the invention has a glycemic index of ranging from 5 to than 55, preferably from 5 to 40, more preferably from 10 to 30, even more preferably from 10 to 25, and in a preferred embodiment from 10 to 20.

Insulinemic Index

The Insulinemic Index (II) is a measurement used to quantify the typical insulin response to various foods. The II is similar to the GI, but is based upon blood insulin levels. This measurement is useful taken together with the Glycemix Index, to check that a low GI is not associated by an exacerbated II. Indeed, some foods can cause a disproportionate insulin response relative to their carbohydrate load. Such foods may be low GI but are not beneficial because of their high insulinemic response.

The II value is measured with the GI value measured by the same standard method as disclosed above for the GI measurement.

The II is the Area Under Curve (AUC) of blood insulin level after consumption of the test food divided by the AUC of blood insulin level after ingestion of the glucose solution and multiplied by 100.

According to the present invention, an Insulinemic Index is considered low when equal or below 60. In a preferred embodiment, the biscuit of the invention has an insulinemic index of less or equal than 60, preferably less than 40, more preferably less than 30.

In particular, the biscuit of the invention has an insulinemic index of ranging from 5 to than 60, preferably from 5 to 40, more preferably from 10 to 30.

In a more preferred embodiment, the biscuit according to the invention has a glycemic index of less or equal than 55, preferably less than 40, more preferably less than 30, even more preferably less than 25, and in a preferred embodiment, less than 20 and/or an insulinemic index of less or equal than or equal 60, preferably less than 40, more preferably less than 30.

In a particular embodiment, the ratio of the insulinemic index over the glycemic index of the biscuit according to the invention is equal or less than 1.0, preferably less 0.9, more preferably less than 0.8, even more preferably less than 0.7, and in a preferred embodiment, less than 0.6.

Water Activity (Aw)

The biscuits according to the invention are "dry products", that is to say that they preferably have a Water Activity (Aw) defined as the ratio of the partial pressure of water vapor surrounding the biscuit related to that of the saturated vapor pressure of water at the same temperature, of less than 0.4.

In a preferred embodiment, the biscuits according to the invention have a water activity between 0.05 and 0.4, and preferably around 0.2.

The biscuits of the invention can be filled with any suitable ingredient or filling. In this case, the Aw value is measured on the initial biscuit, excluding the filling.

Water (Moisture Level)

The biscuit according to the invention can preferably have a residual moisture corresponding to the amount of water in the total finished product, ranging from 0.5 to 5% by weight, relative to the total weight of the biscuit, and more preferably from 1 to 4% by weight. Moisture content is determined by oven desiccation according to NF ISO 712.

Guar Gum

The biscuit of the present invention comprises at least a native guar gum.

In a particular embodiment, the native guar gum used in the biscuits of the invention is in a rod-like form.

Guar gum is obtained from the seeds of the leguminous plant called *Cyamopsis tetragonolobus*. The worldwide consumption of guar gum as a food texturing agent is about of 45 000 metric tons. The fiber status of guar gum has been widely recognized by different Public Health Authorities, including AFSSA in 2002 (SA-0070).

In the present application, the term "seeds of guar" refers to the seeds issued from *Cyamopsis tetragonolobus*. The seeds of guar include the hull, the germ, and the guar splits or endosperm halves. The seeds of guar are generally composed of 35 to 40% by weight of the endosperm, 42 to 47% by weight of the germ, and 14 to 17% by weight of the bark. The guar splits comprise about 68 to 80% galactomannans, about 10% insoluble fibers, about 5% to 15% moisture and 4 to 6% by weight of protein material.

The term "native guar" refers to galactomannan-type macromolecular chains issued from the endosperm (or split) of the guar, and having not undergone any chemical modification such as partial hydrolysis or grafting.

"Native guar" can be obtained according to the following well-known process:
 de-hulling of the guar seeds,
 removing of the germ to recover the guar splits
 washing the split
 milling to a final particle size.

The native guar consists of a (1,4)-β-D-mannopyranose backbone with branchpoints from their 6-positions linked to α-D-galactose (i.e 1,6-linked-α-D-galactopyranose), which may be described chemically as galactomannan (Dea, I. C. M. and Morrison, A., 1975, *Advances in Carbohydrate Chemistry and Biochemistry*, 31, 241). There are, in average, 2 mannose residues for every galactose residue.

The term "guar gum" refers to a product mainly consisting of native guar, under a "guar powder" or "guar flour" form, obtained from the endosperm of guar.

Until now, the direct use of guar flour in a dry state is avoided. Indeed, safety issues have been observed for guar gum pills and tablets. In the mid-1980s, 26 domestic reports of suspected adverse reactions from the guar gum ingestion such as esophageal obstruction, small bowel obstruction, or even death after oral ingestion, were reported either to the Australia Adverse Drug Reaction Advisory Committee, or in American literature in form of case reports of esophageal obstruction.

Surprisingly, the guar according to the present invention does not swell immediately after the oral ingestion and can therefore be safely introduced in dry biscuits.

Additionally, the introduction of the specific guar in a biscuit does not impact the mouth-feel or the organoleptic properties of the final product and does only require minor modifications of the processing parameters, if any.

Therefore, guar flour known in the prior art and used as a thickener is very different from the specific guar of the invention, and should not be considered as a valid alternative to the guar of the invention.

In the same manner, the specific guar particles used in the present invention are different from agglomerated guar particles obtained by compressing or sticking fine guar flour (i.e. resulting from a grinding or a mixing of natural guar into powder) particles such as the one disclosed in document U.S. Pat. No. 4,871,557. Indeed, agglomerated guar will dissolve quickly in the mouth upon mastication, just like guar flour, causing swelling and occlusion problems, and remains unusable in dry foodstuffs at high dosage.

In a preferred embodiment, the guar used in the present invention may be a high viscosity (i.e. high molar mass) guar gum. The molar mass of the guar of the invention was measured by size-exclusion chromatography coupled with light scattering and refractometry.

In a preferred embodiment, the guar used in the present invention has a molar mass ranging between $1 \cdot 10^5$ to $3 \cdot 10^6$ g/mol, preferably between $5 \cdot 10^5$ and $3 \cdot 10^6$ g/mol and more preferably around $2 \cdot 10^6$ g/mol.

Such a molar mass is characteristic from guar containing native galactomannan, i.e. native guar gum.

It is expected, in the context of the present invention, that the higher the molar mass of the guar gum is, the lower the GI and/or II.

The term "rod-like form guar gum" is directed to guar gum in a particulate form having a length longer than its width.

The obtained specific guar gum of the invention consist of anisotropic particles having a length between 0.25 and 8 mm, a width between 0.18 and 2 mm and an average length to width ratio between 1.8 and 6.

Preferably, the guar gum used in the biscuits of the invention have a length between 0.25 and 8 mm, a width between 0.18 and 2 mm and an average length to width ratio around 2.8.

In a preferred embodiment, the guar particles have an average length ranging from 1.3 and 4.2 mm, preferably from 1.7 to 3.2 mm and more preferably around 2.6 mm.

In another preferred embodiment, the guar particles have an average width ranging from 0.6 to 1.3 mm and more preferably around 0.9 mm.

In another preferred embodiment, the guar particles have an average length to width ratio ranging from 2 and 5, preferably ranging from 2.3 and 4, and more preferably around 2.8.

These particles are advantageously strongly anisotropic, as opposed to standard guar flour.

The particle size distribution of guar according to the invention can be obtained according to the following method. Particles of guar are put onto a black sheet of paper and ten pictures are taken, using a stereomicroscope. The micrographs are then analysed using an Image Analysis Software (Visilog 6.4). Each particle is fitted into a rectangle and the following parameters are extracted: length (L, in microns), width (W in microns) and sphericity (no unit), which corresponds to the length to width ratio (L/W) and allows to distinguish between isotropic and anisotropic particles. The average number of guar particles to be analysed by this method should be at least 500 to obtain a representative average, and preferably about 750.

The distribution of length, width and length to width ratio were further analysed using JMP software (release 6.0, SAS) which yielded the quantiles and moments (average and standard error of mean) of the distribution. The average values given values are number-averaged.

In order to show the difference between the specific guar according to the invention, the same procedure was applied to known guar powders in the form of flour or granulates. The stereomicroscope was however replaced by an optical microscope and the black paper by a glass blade covered with oil. Four different types of known guar particles have been measured and analysed: fine guar particles (HI-GRAN-F series of Hindustan Gum), standard guar particles (M225 of Danisco), coarse guar particles (HIGRAN-C series of Hindustan Gum), and Guarem™, a granulated guar from Orion Pharma (Espoo, Finland). The tables indicate the number-averages and the standard errors of mean.

|  | Average length (microns) |
|---|---|
| Fine guar (HIGRAN-F series, Hindustan Gum) | 52 ± 2 |
| M225, Danisco | 59 ± 1 |
| Coarse guar (HIGRAN-C series, Hindustan Gum) | 150 ± 10 |
| Guar of the invention (HIGRAN-G series, Hindustan Gum) | 2585 ± 43 |
| Guarem ®, Orion Pharma | 754 ± 12 |

|  | Average Width (microns) |
|---|---|
| Fine guar (HIGRAN-F series, Hindustan Gum) | 28 ± 1 |
| M225, Danisco | 40 ± 1 |
| Coarse guar (HIGRAN-C series, Hindustan Gum) | 95 ± 6 |
| Guar of the invention (HIGRAN-G series, Hindustan Gum) | 925 ± 43 |
| Guarem ®, Orion Pharma | 478 ± 6 |

|  | Average length/width ratio |
|---|---|
| Fine guar (HIGRAN-F series, Hindustan Gum) | 1.77 ± 0.02 |
| M225, Danisco | 1.48 ± 0.01 |
| Coarse guar (HIGRAN-C series, Hindustan Gum) | 1.65 ± 0.02 |
| Guar of the invention (HIGRAN-G series, Hindustan Gum) | 2.79 ± 0.03 |
| Guarem ®, Orion Pharma | 1.56 ± 0.01 |

The guar of the present invention is obtained by the following process:
  de-hulling of the guar seeds,
  removing of the germ to recover the guar splits
  washing the split
  rolling or laminating the split, for example between two rollers, to obtain the guar particles having a size according to the invention.

The guar gum used in the biscuits of the present invention is not obtained by grinding the guar seeds to powder, for example as disclosed in document U.S. Pat. No. 4,871,557, but only by modifying the original shape of the guar seeds into a guar having a length between 0.25 and 8 mm, a width between 0.18 and 2 mm and an average length to width ratio between 1.8 and 6.

The biscuit of the invention can comprise between 1 and 20% by weight, relative to the total weight of the biscuit, of guar gum, preferably between 3 and 18% by weight, and more preferably between 6 and 15% by weight.

Additional Fibers

Dietary fibers are usually divided according to whether they are water-soluble or not. Both types of fibers are present in all plant foods, with varying degrees of each according to a plant's characteristics.

The guar gum contained in the biscuit according to the present invention is a viscous soluble fiber. Besides guar gum, the biscuits of the invention may comprise other viscous soluble fibers and optionally viscous insoluble fibers, and/or non-viscous soluble fibers.

In a preferred embodiment, the biscuit comprises a mixture of insoluble fibers, viscous soluble fibers and non-viscous soluble fibers.

Insoluble fibers swell in water and show some water-binding properties that help to increase bulk, soften stool and shorten transit time through the intestinal tract.

Sources of insoluble fiber include whole wheat, oat, barley, rye, rice, corn, and especially the bran of these cereals as well as fruit (apple, citrus, prune, mango, fig, etc), vegetables (tomato, carrot, celery, etc) or cocoa.

For the purpose therein, "soluble fibers" means dietary fibers which are water soluble. Soluble fibers generating no or a low viscosity increase after dissolution in an adequate amount of water are referred to as "non-viscous soluble fibers". Non-viscous soluble fibers can either have an average molar mass Mw of less than $3 \cdot 10^4$ g/mol such as fructo-oligosaccharides, galacto-oligosaccharides, xylo-oligosaccharides, manno-oligosaccharides, polydextrose, resistant dextrins, cyclo-dextrins, or a higher molar mass when highly branched and having a compact conformation (hence a low hydrodynamic volume), such as acacia gum.

Alternatively, some other soluble fibers are able to increase the viscosity of water significantly at moderate dosage and are called "viscous soluble fibers". Viscous soluble fibers additional to guar gum include, for example, other galactomannans (locust bean gum, tara gum, fenugreek), glucomannans or konjac flour, psyllium, xanthan, alginates, pectins, beta-glucans from oat or barley, arabinoxylans from wheat, chemically modified cellulosics, which have molar mass between $3 \cdot 10^5$ and $3 \cdot 10^6$ g/mol, and more preferably between $5 \cdot 10^5$ and $2 \cdot 10^6$ g/mol. Some specific mixtures of fibres having synergistic effect in terms of viscosity (e.g. xanthan/locust bean gum, xanthan/glucomannan, etc.) may also be considered as viscous soluble fibers.

In a preferred embodiment of the invention, the biscuit comprises more than 6% by weight, relative to the total weight of the biscuit, of fibers, preferably from 6 to 30% by weight, more preferably from 6 to 25% by weight, more preferably from 12 to 25% by weight, and even more preferably from 15 to 25%, guar gum being comprised in said fibers.

Sugar and Sugar Derivatives

The biscuit of the invention may also comprise a small amount of sugars and/or sugar derivatives.

The expression sugar(s) is understood to mean, for the purposes of the present invention, any sweetening monosaccharide such as glucose- or dextrose-, fructose, galactose, mannose, and the like, or disaccharide such as sucrose, lactose, maltose, etc.

Preferably, the sugar introduced in the biscuits according to the invention can be chosen among sucrose, glucose, fructose, maltose, lactose, or any mono and disaccharide blend found in invert sugar, glucose syrups, honey, or mixtures thereof.

The sugar may also be added to the biscuits of the invention in the form of a fine powder such as confectioner's sugar.

Sugar derivatives can also be introduced in the biscuit of the invention. Polyols such as maltitol, sorbitol and isomalt are well known sugar derivatives, and are often used in food products as sugar replacers since they have sweetening properties and comparable technological properties (colligative properties, viscosity, crystallisation, etc. . . . ).

In a preferred embodiment, the biscuits according to the present invention comprise less than 25% by weight, relative to the total weight of the composition, of sugar or sugar derivatives, preferably from 2 to 25% by weight, more preferably from 5 to 20% by weight, and even more preferably from 10 to 18% by weight.

The term "fructose" is intended to mean the fructose introduced in the biscuit, excluding fructose obtained after chemical modification of other sugars during digestion, such as hydrolysis of sucrose.

In preferred embodiment, the biscuits of the present invention comprise less than 25% by weight, relative to the total weight of the composition, of fructose, preferably from 2 to 25% by weight, more preferably from 5 to 20% by weight, and even more preferably from 10 to 20% by weight.

In a more preferred embodiment, the biscuits of the present invention comprise less than 25% by weight, relative to the total weight of the biscuit of fructose, preferably less than 10% by weight and/or less than 25% by weight, relative to the total weight of the biscuit of polyols, preferably less than 10% by weight, and even more preferably both.

Fats

Biscuits according to the present invention may additionally comprise fats that can either be saturated or unsaturated.

The term "fat" as used herein is synonymous with the term "lipid". Suitable sources of the fat source include vegetable, dairy, animal and/or marine fat sources. Useful herein are fats and oils that are conventionally used in food products, particularly biscuits and cereal snacks.

Any natural fat is a blend of saturated and unsaturated fatty acids.

Saturated fatty acids do not contain any double bonds or other functional groups along the chain.

Saturated fatty acids form straight chains and, as a result, can be packed together very tightly, and form crystallites with interesting interfacial properties such as air bubble stabilization.

Unsaturated fatty acids are fatty acids comprising one or more alkenyl functional groups and can have either a cis or a trans configuration.

A cis configuration means that adjacent hydrogen atoms are on the same side of the double bond. A trans configuration, by contrast, means that the next two hydrogen atoms are bound to opposite sides of the double bond. As a result, the trans configuration unsaturated fatty acids do not cause the chain to bend much, and their shape is similar to straight saturated fatty acids.

Fats such as oils and solid fats can be used herein as well as blends thereof. In the biscuit industry, particularly useful oils include, for example, non-hydrogenated and/or partially hydrogenated oils such as palm oil, palm kernel oil, coconut oil, rapeseed oil, canola oil, corn oil, safflower oil, sunflower oil, soybean oil, cottonseed oil, flaxseed oil and their fractions.

Dairy (butter), animal (e.g., lard, beef tallow) and marine (e.g., fish oil) fat sources are generally less desired, but are also used, especially butter.

Oils having a melting point above room temperature generally are more convenient to process with and are used in most of biscuit formulations.

In a preferred embodiment, fats can be chosen from rapeseed oil, canola oil, and a mixture thereof.

Partially digestible and non-digestible synthesized triglycerides or natural lipids may also optionally be used.

For the human body, the most important fatty acids are polyunsaturated fatty acids which are the parent compounds of the omega-6 and omega-3 fatty acid series. They are essential in the human diet because there are not synthesized by human body. Humans can easily make saturated fatty acids or monounsaturated fatty acids with a double bond at the omega-9 position, but do not have the enzymes necessary to introduce a double bond at the omega-3 position or omega-6 position.

Omega-3 fatty acids are polyunsaturated fatty acids wherein the first double bond of the chain is located on the third carbon situated after the methyl group.

It is known, moreover, that trans fatty acids (TFA) and saturated fatty acids (SFA) raise the bad cholesterol (LDL), lower the good cholesterol (HDL) and may increase triglycerides and lipoproteins(a) (also called Lp(a)).

For these reasons, in a preferred embodiment, the biscuits according to the present invention comprise less than 20% by weight, relative to the total weight of the composition, of fats, preferably from 5 to 20% by weight, preferably from 10 to 16% by weight.

In another preferred embodiment, the maximum amount of trans fatty acids and saturated fatty acids in the biscuit according to the invention should not exceed, respectively 0.1% and 2% by weight, relative to the total weight of the biscuit.

Preferably the total amount of trans fatty acids and saturated fatty acids in the biscuit should not exceed 5%, preferably 3% and more preferably 1.6% by weight, relative to the total weight of the biscuit.

In a more preferred embodiment, the maximum amount of trans fats and saturated fatty acids should not exceed 1% and 20% by weight, relative to the total weight of the fats contained in the biscuit.

In an even more preferred embodiment, the amount of polyunsaturated fatty acids, parent compounds of the omega-3 fatty acid series, can be ranging from 0.2 and 1% by weight, relative to the total weight of the composition, preferable from 0.6 to 0.95% by weight.

Cereals

The biscuit according to the invention can comprise cereals.

Cereal grains supply most of the daily required food energy and are also a significant source of protein.

Cereal grains can be chosen among wheat, oat, barley, rye, spelt, maize, rice, sorghum, millets, triticale, buckwheat, fonio, teff, quinoa, and a mixture thereof.

Whole grains are good sources of dietary fiber, essential fatty acids, and other important nutrients. Whole grains are cereal grains that retain the bran and germ as well as the endosperm, in contrast to refined grains, which retain only the endosperm.

Common whole-grain products include oatmeal, popcorn, brown rice, whole-wheat flour, sprouted grains, and whole-wheat bread.

In order to obtain a good nutrition profile biscuit according to the invention, the amount of cereal should preferably be greater than 30% by weight, relative to the total weight of the biscuit, preferably from 30 to 70% by weight, more preferably from 40 to 70% by weight and even more preferably from 50 to 65% by weight.

In a particularly preferred embodiment, the biscuit according to the invention can comprise from 40 to 70% by weight, relative to the total weight of the biscuit, of cereal, and preferably from 40 to 80% by weight, relative to the total weight of the biscuit, of whole grains.

Flour

Flours are extracted from the endosperm of cereals and contain about 80% starch, 10% proteins and 10% water. They are the main component of the biscuit.

In a preferred embodiment of the invention, the biscuit comprises starch, and preferably starch having its native pseudo-crystalline structure slightly disrupted or not disrupted at all.

All plant seeds and tubers contain starch which is predominantly present as two polysaccharides: amylose and amylopectin. Depending on the plant, starch may contain between 0 to 70 percent amylose and 30 to 100 percent amylopectin.

Starch is a white powder, and depending on the source, may be tasteless and odorless.

Starch supplies most of the daily required food energy as it is the main component of cereals. Commercial starches include wheat starch, cornstarch, arrowroot, potato starch, sago and tapioca.

In its native state, starch has a pseudo-crystalline structure. In presence of water combined with a thermal treatment such as occurring during baking, its native pseudo-crystalline structure is partially disrupted.

In the specific case of low GI biscuits, the increase of the hydration of the dough usually required by the incorporation of water-binding fibers favours the disruption of the native pseudo-crystalline structure of the starch powder. As a result, starch becomes more easily accessible to $\alpha$-amylases during the digestion in the small intestine, and is more quickly assimilated by the organism. This results in an increase of the glycemic and insulinemic index and a loss of the clinical benefit of such products.

It was surprisingly observed that the introduction of specific guar gum according to the invention in low GI biscuits did not require an increase of the hydration of the dough when incorporated at less than 13% and only a limited increase above. It is then possible to obtain low GI biscuits containing simultaneously guar in its native pseudo-crystalline structure or slightly disrupted and a viscous soluble fiber or guar gum. Said biscuits provide particular low GI index.

Salt

In a preferred embodiment, the good nutrition profile biscuits according to the present invention can comprise less than 500 mg per 100 g of the finished products of sodium.

Additional Components

The products according to the invention may comprise any other well-known additional components necessary to the composition of a biscuit, such as for example milk, eggs, emulsifiers, fruit chips, chocolate drops, flavours, colouring agent, leavening agents among which ammonium bicarbonate, sodium bicarbonate, sodium pyrophosphate and the like.

Kinetics of Dissolution

The kinetics of dissolution of guar gum in water has been described in several studies, using viscosity as an indirect indicator of the hydration process (O'Connor, N, Tredger, J. and Morgan, L., Diabetologia, 1981, 612-615; Ellis, P. R. and Morris, E. R., Diabetic Medicine, 1991, 8, 378-381; Wang, Q., Ellis, P. R. and Ross-Murphy, S. B., Carbohydrate Polymers, 2006, 64, 239-246; Parvathy, K. S., Susheelamma, N. S, and Tharanathan, R., Food Hydrocolloids, 2007, 21, 630-637). There are a number of similarities between these studies:

(a) Guar gum is globally used at a concentration of 1% (w/w or w/v), preferably with a correction of the moisture content of guar gum (i.e. 1 g of dry matter),
(b) The solvent is water (distilled to tap),
(c) The dissolution process is followed at ambient temperature (22° C. to 25° C.),
(d) The guar is first dispersed by vigorous whisking (O'Connor et al, 1981), or dispersed into a rapidly swirling vortex generated by a magnetic stirrer for 1 to 2 minutes (Ellis and Morris, 1991; Wang et al, 2006; Parvathy et al, 2007) then left to hydrate at low shear conditions, interrupted by regular viscosity measurements.
(e) viscosity is measured using Brookfield Synchro-Lectric RVT viscometer, and a spindle 4 at 20 rev/min (O'Connor et al, 1981; Ellis and Morris, 1991; Wang et al, 2006) or 30 rev/min (Parvathy et al, 2007)

There is however a number of hurdles that prevents to reproduce exactly the same hydration protocol. Indeed, O'Connor et at (1981), Ellis and Morris (1991), Wang et at (2006) used a specific mixing box constructed by the King's College (London, UK) and fitted inside an incubator to allow good control of experimental temperature. The guar dispersion was prepared and sealed in a screw-top glass jar, which was then rotated end-over-end at pre-set speed during the hydration process. The speed was estimated as the minimum needed to promote dispersion and hydration of guar gum and varied between 6 rpm to 10 rpm depending on the sample. An aliquot of approximately 2 ml was taken from the batch solution at regular intervals for viscosity measurement. Such mixing box is, to our knowledge, not commercially available. Another hurdle is the preliminary dispersion of the guar in the vortex generated by a magnetic stirrer, again difficult to reproduce in exactly the same conditions as in the studies, and even in a completely reproducible manner, when using samples with very different hydration rates. Another limitation is the use of the Brookfield viscosimeter, which is a low sensitivity equipment, making difficult to monitor the start of the hydration process. The spindle used was described in the studies, but depending on the dimensions of the vessel and the extent of the gap, the shear rate profile can vary significantly. Last, the hydration times are usually limited to about 5 hours, which is too short for the guar of the invention (some authors make an ultimate viscosity measurement after 24 hours, but there is a lack of information regarding the evolution of viscosity between 5 hours and 24 hours).

Method for Measuring the Kinetics of Dissolution of the Guar Gum According to the Invention or any Commercial Guar Gum.

Experimental Equipment

In order to characterize the guar of the invention or any commercial guar, the method described in details in Patent Application FR 0857128 was used. This Application relates to a measurement method of the consistency generated by a food in the stomach and small intestine. This method uses a combination of a rheometer and a helix-type stirrer to homogenise the mixtures modelling the gastric or intestinal bolus and to measure their viscosity simultaneously.

To measure the kinetics of dissolution of guar gums, tests were conducted using the following conditions (also described in Ellis, P. R. and Morris, E. R., Diabetic Medicine, 1991, 8, 378-381):

Hydrating 1% w/w of guar (corresponding to about 4.95 g to 5.1 g of guar depending on moisture content) in 445 ml of demineralised water at a controlled temperature of 25° C.

Adapting (as follow) the stirring conditions for the guars of the invention, and Using the equipment described in the examples 1 and 2 of FR 0857128, with the following hydration procedure:

(a) Rotating of the geometry at 406 rpm for 1 minute, generating an average shear rate of 150 s$^{-1}$, in water in order to create a steady vortex.
(b) Dispersing of the guar gum during 2 minutes in a vortex generated by the rotation of the helix stirrer at 406 rpm, which generated an average shear rate of 150 s−1.
(c) Hydrating gently of the guar gum during 15 h with a constant rotation of 27 rpm, yielding an average shear rate of 10 s$^{-1}$.
(d) Carrying out a flow curve from 0.01 s$^{-1}$ to 150 s$^{-1}$ in 3 minutes, followed by a return curve from 150 s$^{-1}$ to 0.01 s$^{-1}$ in 3 minutes.

With this equipment, mixing and viscosity measurement are carried out simultaneously and there is no need to interrupt the mixing to take aliquot samples.

No operator is needed to make viscosity measurements, such that the monitoring can be done continuously over long periods of time (15 h in average, but some measurements were performed during 40 h)

Guar Tested

Guar gum used according to the present the invention (HIGRAN-G series from Hindustan Gum) was tested and was as well sieved at 2 mm, 1.25 mm, 1 mm, 0.8 mm, 0.63 mm and 0.4 mm.

Guar gum of the invention (HIGRAN-G series from Hindustan Gum) was sieved using a RETSCH AS 200 CONTROL equipped with a series of sieves: 2 mm, 1.25 mm, 1 mm, 0.8 mm, 0.63 mm and 0.4 mm. A total of 8 kg of HIGRAN G was sieved to obtain the following distribution:

| Sample | % of the distribution (in mass) |
| --- | --- |
| <400 microns | 0.3% |
| 400 microns | 3.3% |
| 630 microns | 16.3% |
| 800 microns | 19.4% |
| 1000 microns | 59.0% |
| 1250 microns | 1.7% |

The fractions sieved were then analysed by image analysis using the procedure described.

Viscosity Measurements

Figure 3:
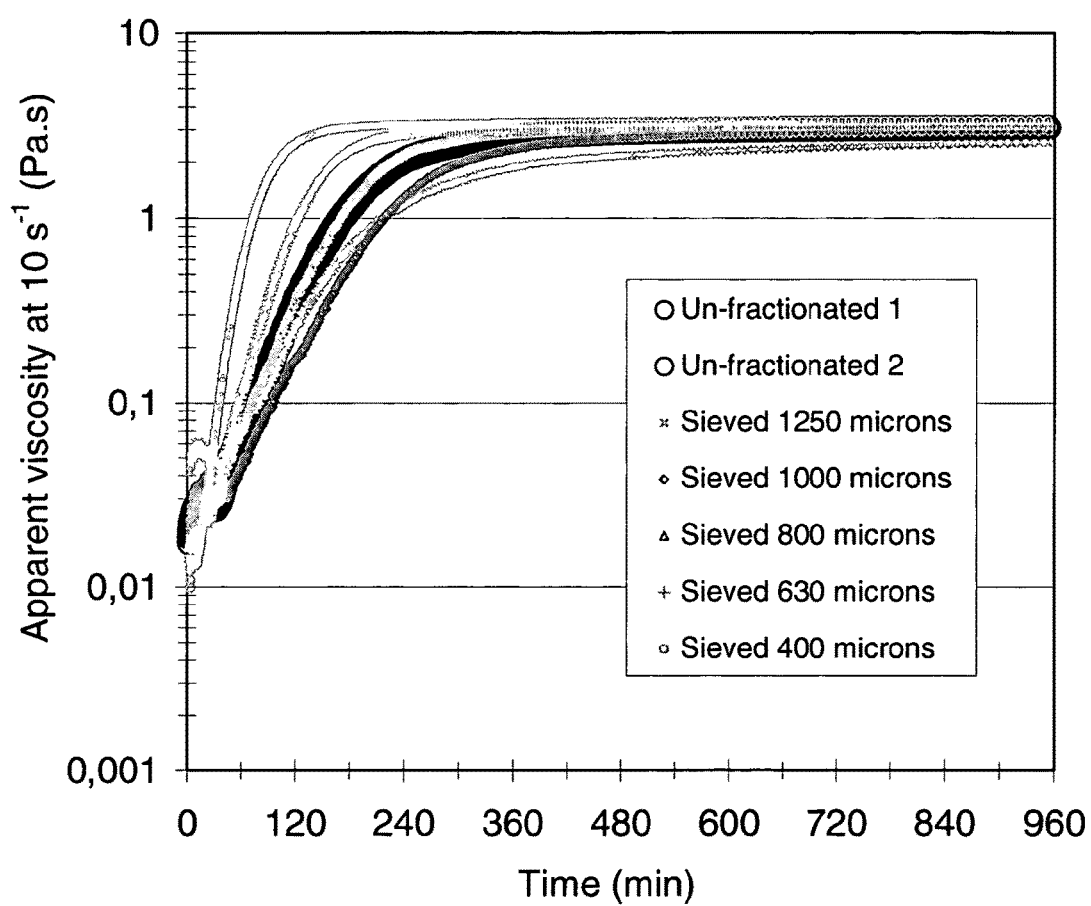
FIG. 3 is a graph showing apparent viscosity values for the inventive guar gum and the same guar after sieving.

FIG. 3 shows the evolution of the apparent viscosity at 10 s$^{-1}$ during phase (c) (i.e. starting from T=3 minutes (end of phase (b)), up to 16 h) for guar gum of the invention (HIGRAN-G series from Hindustan Gum) and the same guar after various sieving.

FIG. 3 shows the very progressive dissolution of the guar of the invention. The pseudo-increase in viscosity at the start of the test is due to particle sedimentation. In order to be comparable with prior art, a low shear rate is used for the viscosity measurement. Due to this low shear rate, the large and dense particles (having a volumic mass of about 1.4 to 1.5 kg/l) sedimented first and increased the viscosity by the generating friction with the bottom bar of the helix-geometry. After some time, the particles swelled and were finally pumped back in the solution, to form after 15 h a rather homogenous solution. Some particles or dark spots remained visible but appeared to have no impact on viscosity. Homogenising the solutions with an Ultra-Turrax mixer, as used in Ellis, P. R. and Morris, E. R., Diabetic Medicine, 1991, 8, 378-381, did not modify the viscosity.

Results:

The evolution of the viscosity of the HIGRAN G guar was first tested for a 48 h duration.

After 15 h; the viscosity reached a plateau value of 3.081 measured with the equipment previously described (combination of a rheometer and a helix-type stirrer to homogenise the mixtures modelling the gastric or intestinal bolus and to measure their viscosity simultaneously disclosed in FR 0857128). Between the 47$^{th}$ h and 48$^{th}$ h, said viscosity hardly evolved, increasing up to 3.228 Pa·s.

The evolution of the viscosity of the HIGRAN G guar was tested a second time during 15 h and the plateau viscosity value reached at 15 h was 3.077, showing the good reproducibility of the test.

This corresponds to a viscosity increase of about 0.005 Pa·s per hour between 15 h and 48 h, which confirms that the standard test duration of 15 h is representative of a complete hydration (i.e. complete development of the viscosity).

Therefore, the plateau viscosity for the other guar tested was the viscosity value obtained at the end of the test (i.e. between 14 h and 15 h).

The time $t_{0.8}$ is the hydration time necessary to reach the $V_{0.8}$ viscosity value corresponding to 80% of the plateau viscosity.

This hydration time necessary to reach the $V_{0.8}$ viscosity value corresponding to 80% of the plateau viscosity is the parameter used to quantify the kinetics of dissolution of guar gums in the present invention. This parameter is disclosed in Wang, Q., Ellis, P. R. and Ross-Murphy, S. B., in their article Carbohydrate Polymers, 2003, 53, 75-83. In other words, $t_{0.8}$ is the time at which the viscosity $V_{0.8}$ (corresponding to 80% of the plateau viscosity=0.8×Plateau viscosity value) is obtained.

For instance, the plateau viscosity value of the HIGRAN G guar curve after 15 h was 3.08 Pa·s). Therefore, $t_{0.8}$ of the HIGRAN G guar is of 0.8×3.88=2.46 Pa·s, which is obtained after 292 minutes (corresponding to $t_{0.8}$) as calculated with the method described below.

Therefore, another object of the present is a biscuit comprising a guar gum having a $t_{0.8}$ (hydration time necessary to reach the $V_{0.8}$ viscosity value corresponding to 80% of the plateau viscosity obtained at 25° C.) ranging from 130 minutes to 390 minutes, preferably from 216 to 390 minutes.

This time $t_{0.8}$ is calculated according to the method described hereunder.

More precisely, the analysis proposed by Wang, Q., Ellis, P. R. and Ross-Murphy, S. B., Carbohydrate Polymers, 2006, 64, 239-246 was used to obtain the shift factors, necessary to calculate the $t_{0.8}$.

A master curve is carried out by
(a) Normalizing the viscosity of each guar tested by dividing the viscosity value in function of the time by the plateau value, obtained after 15 h (or more than 15 h when the viscosity value obtained after 15 h is not representative of the viscosity value after 48 h, which was not the case for the guars tested), and
(b) Superimpose the normalized viscosity curves obtained by multiplying the time by a shift factor in order to superimpose the normalized viscosity curves to an arbitrary curve chosen as the reference curve (here the chosen reference curve was the one obtained with the commercial HIGRAN G guar). In the case the curves do not entirely superimpose with each other, the part of the curve corresponding to the increase of the viscosity should be the part superimposed for all the curves.

For instance, for the sample sieved at 400 microns, multiplying the time by 2.25 (shift factor) allowed both curves (commercial HIGRAN G guar and guar sieved at 400 microns) to superimpose.

This indicates that the hydration process follows in essence the same pattern but is accelerated by a factor 2.25 when the HIGRAN G guar is previously sieved at 400 microns in comparison to the un-fractionated sample (HIGRAN G guar commercially available). The curve resulting from this superimposition is called a master curve, as illustrated on FIG. 4. The superposition is correct, except at short times, where sedimentation generate artefacts on viscosity values.

The $t_{0.8}$ value for the guar tested was calculated thanks to the shift factors, according to the following Equation 1:

$$t_{0.8}[\text{sieved sample}] = \frac{1}{\text{Shift Factor}} \cdot t_{0.8}[HIGRAN\ G] \quad \text{Equation 1}$$

The shift factors, plateau viscosities and values of $t_{0.8}$ are given in Table A for all the guars tested, as well as the dimensions (L, W and L/W) of the particles:

TABLE A shift factors, plateau viscosities and $t_{0.8}$ values of HIGRAN G guar and sieved samples

| Sample | % in mass, relative to the mass of the Un-fractionated guar | Average L (microns) | Average W (microns) | Average L/W (no unit) | Kinetic Shift factor | Plateau viscosity (Pa · s) | $t_{0.8}$ (min) |
|---|---|---|---|---|---|---|---|
| <400 microns | 0.3% | 1050 | 420 | 2.35 | 5.00 | 2.10 | 63 |
| 400 microns | 3.3% | 2150 | 690 | 3.05 | 2.25 | 3.46 | 140 |
| 630 microns | 16.3% | 2080 | 810 | 2.54 | 1.35 | 3.46 | 234 |
| 800 microns | 19.4% | 2460 | 980 | 2.46 | 1.00 | 3.46 | 316 |
| 1000 microns | 59.0% | 3820 | 1320 | 2.96 | 0.75 | 3.15 | 421 |
| 1250 microns | 1.7% | 4090 | 2200 | 1.9 | 0.95 | 2.62 | 344 |
| Un-fractionated | 100% | 2585 | 925 | 2.78 | 1 | 3.08 | 316 |

This procedure was reproduced on different guar gum samples, with a more spherical morphology: HIGRAN F (fine guar gum), HIGRAN C (coarse guar) and GUAREM. It was again possible to obtain a master curve. The shift factor, plateau viscosity and $t_{0.8}$ are given in Table B, together with morphological characteristics. Values for HIGRAN G are also reminded for comparison.

TABLE B shift factor, plateau viscosity and $t_{0.8}$ values vs. the morphological characteristics of guars tested

| Sample | Average L (microns) | Average W (microns) | Average L/W (no unit) | Kinetic Shift factor | Plateau viscosity (Pa · s) | $t_{0.8}$ (min) |
|---|---|---|---|---|---|---|
| HIGRAN F | 52 | 28 | 1.77 | 46 | 3.15 | 6.9 |
| HIGRAN C (1) | 150 | 95 | 1.65 | 5 | 2.62 | 63 |
| HIGRAN C (2) | 150 | 95 | 1.65 | 5 | 2.10 | 63 |
| GUAREM (1) | 754 | 478 | 1.56 | 2.35 | 1.99 | 134 |
| GUAREM (2) | 754 | 478 | 1.56 | 2.1 | 2.20 | 150 |
| HIGRAN G | 2585 | 925 | 2.78 | 1 | 3.08 | 316 |

Figure 5:
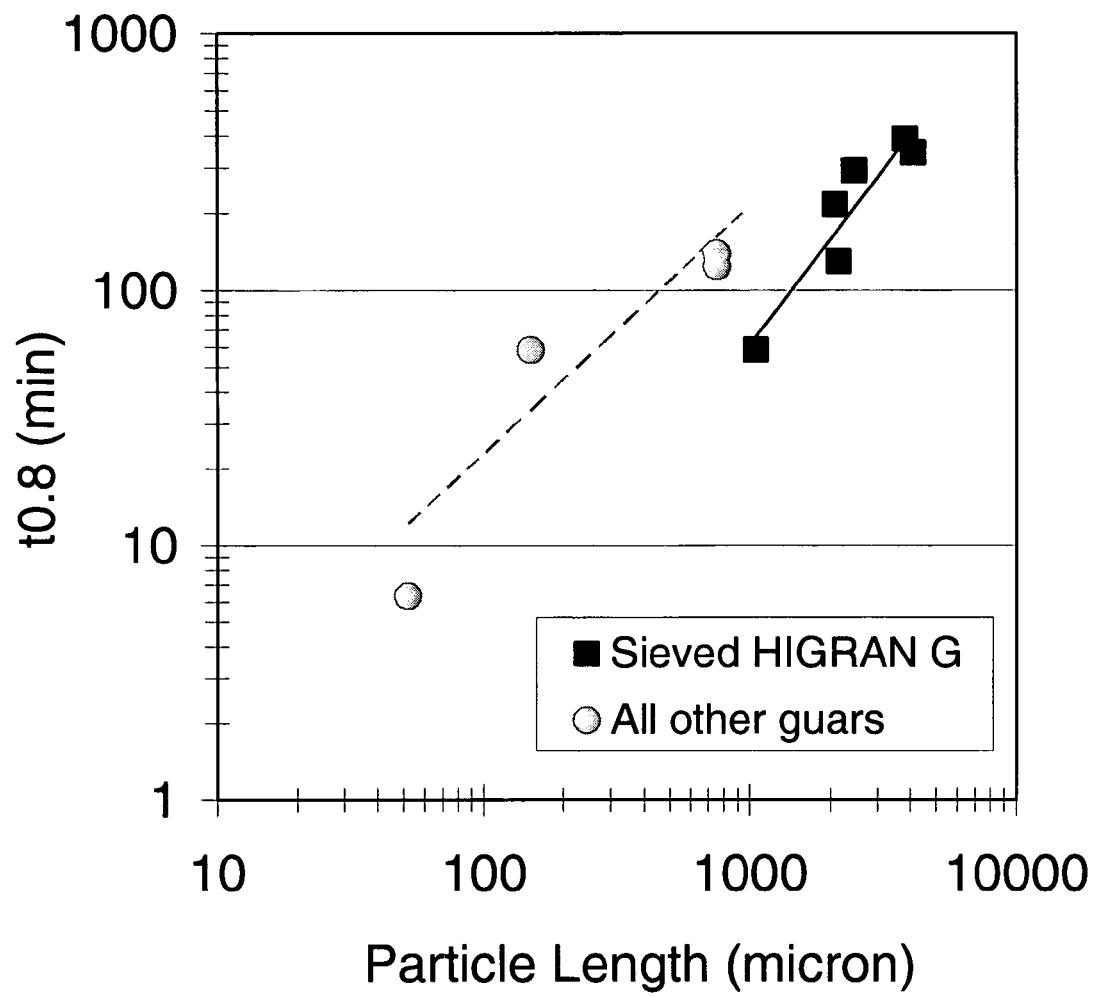
FIG. 5 is a graph showing $r_{0.8}$ as a function of particle length obtained for HIGRAN G and other guar gums.
Figure 6:
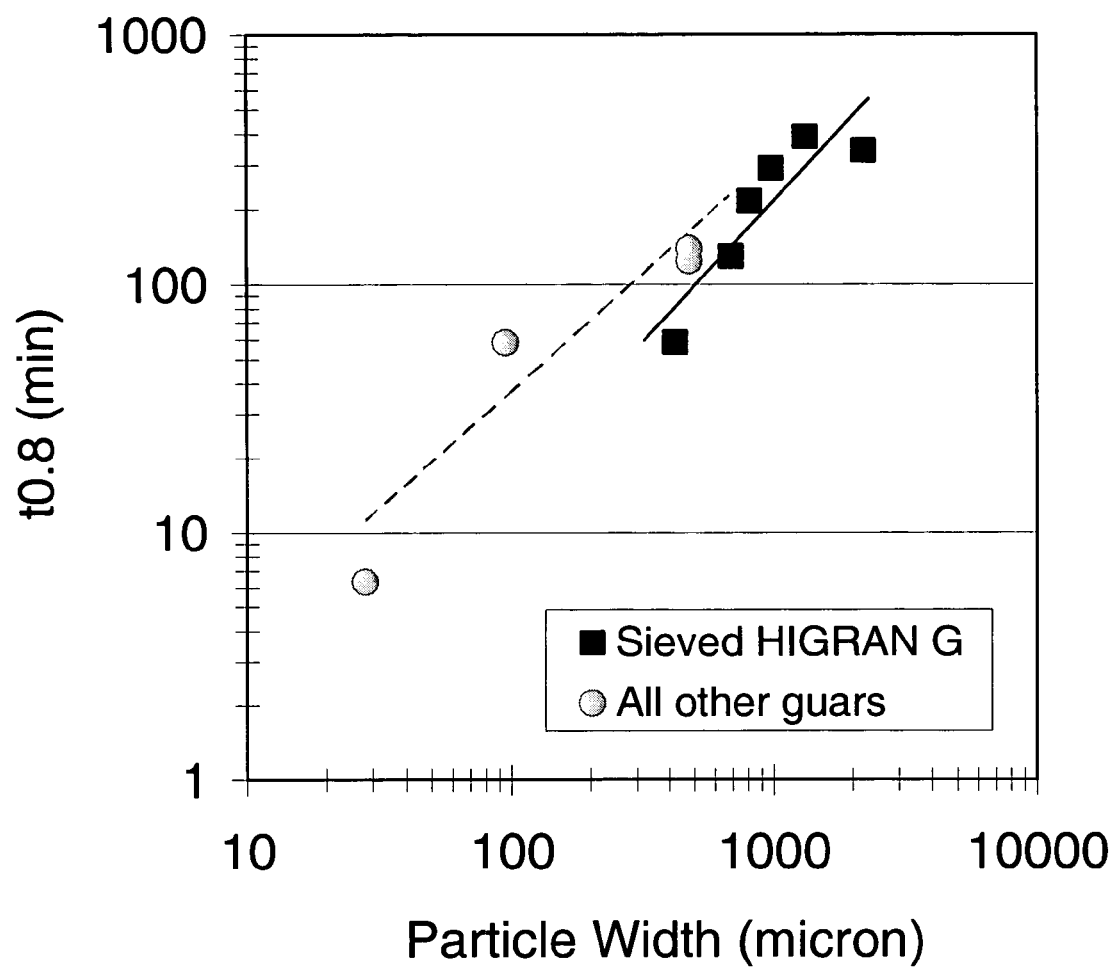
FIG. 6 is a graph showing $r_{0.8}$ as a function of particle width obtained for HIGRAN G and other guar gums.

The comparison of the $t_{0.8}$ obtained for the HIGRAN G (un-fractionated and sieved) and the other guar gums are shown in FIGS. 5 and 6. Since the morphology of these guars was very different, the only way to conclude on the impact of size on hydration rate is to compare both particles dimensions, i.e. their length L (FIG. 5) and their width W (FIG. 6).

The time $t_{0.8}$ seems to vary as a power-law=$t_{0.8}$=a $X^b$, X being the particle length L or width W.

The prior art shows that guar gum must hydrate quickly in order to be physiologically efficient (O'Connor et, 1981). Ellis and Morris (1991) indicate that Glucotard minitablets, with 3 mm thick and 4 mm diameter hydrate very slowly and suggest that it may be the reason why this product has often failed to improve blood glucose response in clinical trials. The guars of the invention have macroscopic dimensions, comparable to Glucotard minitablets but were instead shown to induce a marked improvement in blood glucose and insulin control. Our findings contrast with the prior art, since we show that both glycemic and insulinemic index and gastric emptying can be positively affected by the guar gum of the invention contained in the biscuits, in spite of its slow hydration.

The results shown in FIGS. 5 and 6 suggest one possible element of explanation. Without being bound by any theory, it could be assumed that, due to their peculiar elongated shape, the guar particles proportionally have a higher surface exposed to water vs. spherical particles. During the early stages of hydration, this will help the particles to swell and become softer, which could favour particle break-up, therefore accelerating the global hydration process. By opposition, spherical particles would have a lower surface exposed to water and would mostly hydrate via an erosion process (guar chains progressively leaving the swollen surface of the grain). This may explain why guar of the invention hydrates quicker than a spherical particle of the same size and also why surprisingly strong physiological effects were observed with such a slowly soluble guar.

Method for Measuring the Kinetics of Dissolution of Biscuits According to the Invention or any Commercial Biscuit Experimental Equipment The method used to monitor the kinetics of dissolution of guar gum in the biscuits has been described in Patent Application FR 0857128. The patent application relates to an in vitro measurement method of the consistency generated by a food in the stomach and small intestine. The methods comprises 3 steps: (a) grinding of the food to reproduce the mechanical breakdown performed during chewing, (b) mixing under stirring of the ground food with a solution modelling gastric fluid in a reactor vessel coupled with a rheometer, for a time corresponding to gastric digestion and (c) adjustment under stirring of the reaction mixture to model intestinal digestion conditions for a time corresponding to intestinal digestion, the rheometer being provided with a stirrer used to homogenise the mixture and measure the viscosity thereof simultaneously. The following results were obtained in the conditions defined in examples 1 and 2.

Biscuits containing defined amounts of HIGRAN-G series from Hindustan Gum was first grounded using a kitchen grinder, in order to simulate the mechanical degradation of the biscuit in the mouth during mastication. The conditions of mixing will be adjusted in order to obtain biscuits powders having a D50 and a D90 of about 800 and 1400 microns respectively when measured by laser light granulometry.

50 g of the biscuit powders were then dispersed under high shear rate conditions (150 s-1) in a gastric fluid, composed of 400 ml water acidified to pH=2 with chlorhydric acid 4N and containing 1 g of pepsin (P7000, Sigma Aldrich). After 20 minutes of hydration, pH value had slightly increased and was set back to 2 by addition of chlorhydric acid, and the shear rate was set to $10\ s^{-1}$ in order to monitor the evolution of the viscosity in laminar flow conditions. After 70 minutes, a flow curve was carried out, starting from $0.01\ s^{-1}$ up to $150\ s^{-1}$ in 3 minutes, then coming back to $0.01\ s^{-1}$ in 3 minutes. The reaction fluid was then neutralised to pH 6.3 by addition of sodium hydroxide 4N, and 1.63 g porcine pancreatin (P7545, Sigma Aldrich) and 1.2 g bile salts (B8631, Sigma Aldrich) were added. During this phase, the shear rate was set back to $150\ s^{-1}$ in order to achieve good mixing conditions and an accurate pH control. After 20 minutes of this mixing phase, the shear rate was again set at $10\ s^{-1}$, to monitor the evolution of the viscosity in laminar flow conditions for 90 minutes, before carrying out a flow curve in the same conditions as previously.

Biscuits Tested

The 4 biscuits used in this tests contained guar in an amount of respectively 6%, 13%, 18% (respectively biscuits 1, 2 and 3 of example 4 hereafter) and 20% (corresponding to the biscuit 3 of example 4, in which the amount of guar have been increased to 20%, the only parameter of adjustment being cereals) by weight, relative to the total weight of the biscuit.

Results

Figure 4:
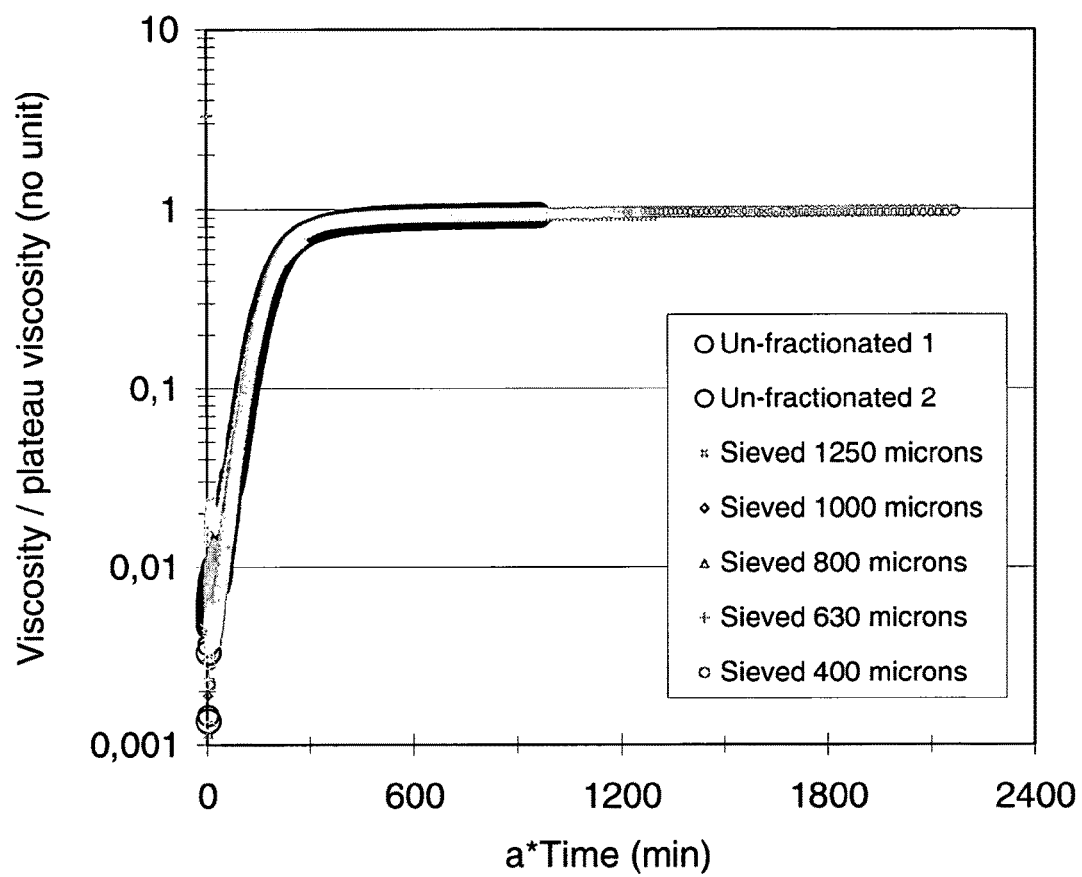
FIG. 4 is a graph showing a master curve obtained by a superimposition of normalized viscosity curves of tested guars to a curve obtained with HIGRAN G guar.

The method used to calculate t0.8 is the same as the one already described for the guar particles.
a) The curve illustrating the viscosity of the biscuit containing the maximum amount of guar (here 20%) is chosen as the reference curve, since at this concentration a clear plateau value was obtained
b) all viscosity vs. time curves were normalised by the plateau viscosity obtained at the end of the test
c) a master curve is then obtained by shifting the normalised viscosity curves of the other biscuits tested so as to superimpose them to the reference curve (here, viscosity curves of biscuits containing 6%, 13% and 18% of guar were shifted to superimpose the curve of the biscuit containing 20% guar, using a specific shift factor, in order to obtain a master curve such as shown in FIG. 4).
c) the $t_{0.8}$ is then calculated according to equation 1

Figure 7:
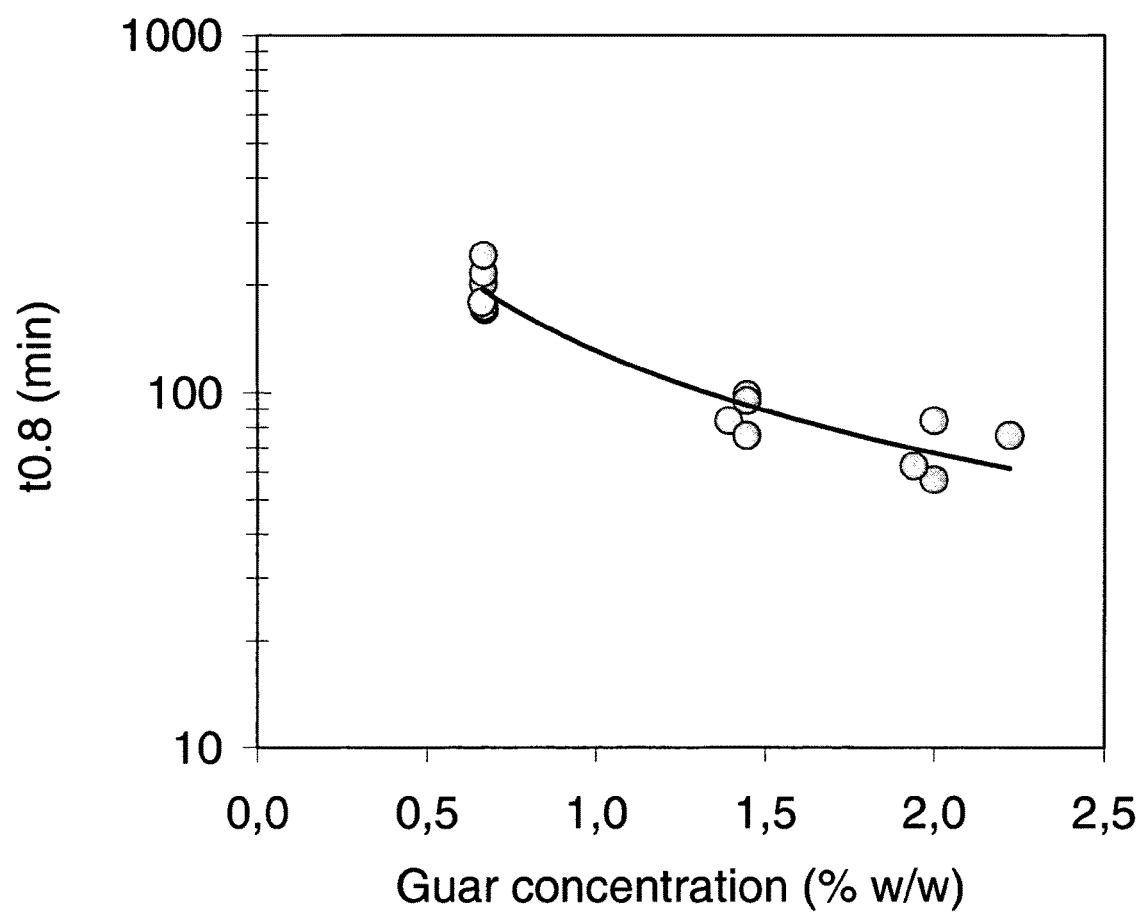
FIG. 7 is a graph of $r_{0.8}$ as a function of guar concentration.

FIG. 7 illustrated the evolution of the time $t_{0.8}$ in function of guar concentration and again, a power-law model can be used to fit the results.

The time $t_{0.8}$ decreases continuously with guar concentration, contrary to the results disclosed by Wang, Q., Ellis, P. R. and Ross-Murphy, S. B., in their article Carbohydrate Polymers, 2003, 53, 75-83. These authors found an increase in $t_{0.8}$ for guar concentrations larger than 1.2%.

The biscuit of the invention can comprise between 1 and 20% by weight, relative to the total weight of the biscuit of guar gum. Therefore, if a serving of 50 g is eaten with 400 ml of liquid, which is the case for a typical breakfast, the guar concentration in the bolus would be between 0.1% and 2.2%. On the basis of this in vitro test, the $t_{0.8}$ would be comprised between 61 and 1060 minutes, using the procedure described above.

Preferably, the biscuit of the invention can comprise from 3% to 18% by weight, relative to the total weight of the biscuits, of guar gum, which provides a $t_{0.8}$ value ranging from 68 and 370 minutes. More preferably, the biscuit can comprise from 6% to 15% of guar gum, which provides a $t_{0.8}$ value ranging from 80 and 193 minutes.

Therefore, a further object of the invention is a biscuit having a $t_{0.8}$ (hydration time necessary to reach the $V_{0.8}$ viscosity value corresponding to 80% of the plateau viscosity obtained at 25° C.) ranging from 61 and 1060 minutes, preferably from 68 to 370 minutes, and more preferably from 80 and 193 minutes Uses of the Biscuits of the Invention The introduction of viscous soluble fibers such as guar gum in biscuits according to the invention generate physiological effects such as a flattening of glycemic and/or insulinemic responses, or reducing blood cholesterol and other blood lipids.

Hence, the present invention can also refers to the use of a biscuit as described herein to generate a low glycemic and/or insulinemic response to the subject consuming it.

According to the invention, a biscuit is considered to "induce a low glycemic response after consumption" when the blood glucose measured following the ingestion of a biscuit according to the invention is lower than the response obtained with the same biscuit containing no guar in a portion containing the same amount of available carbohydrates.

According to the invention, a biscuit is considered to "induce a low insulinemic response after consumption" when the blood insulin measured following the ingestion of a biscuit according to the invention is lower than the response obtained with the same biscuit containing no guar in a portion bringing the same amount of available carbohydrates.

The present invention can also refers to the use of a biscuit as described herein to generate a low glycemic and insulinemic response to the subject consuming it, said subject suffering from diabetes and especially type 2 diabetes or insulino-resistance.

Type-2 diabetes, also called non-insulin-dependent diabetes mellitus (NIDDM), is a metabolic disorder that is primarily characterized by insulin resistance, relative insulin deficiency, and hyperglycemia. Contrary to type 1 diabetes, which is an autoimmune disease that results in the permanent destruction of insulin-producing beta cells of the pancreas, type-2 diabetes is often managed by increasing exercise and dietary modification, and does not require insulin injections.

Whereas this disease used to be seen primarily in adults over age 40, it is now also increasingly seen in children and adolescents, an increase thought to be linked to rising rates of obesity in this age group.

Another object of the invention is the use of guar gum with a length between 0.25 and 8 mm, a width between 0.18 and 2 mm and an average length to width ratio between 1.8 and 6, to decrease insulinemic index of a biscuit when added in the biscuit matrix and/or to decrease glycemic index of a biscuit when added in the biscuit matrix, preferably both.

It is as well known that the various soluble fibres decrease the LDL-cholesterol concentrations. This can be explained by a decrease in cholesterol absorption due to the high viscosity of the fibre that alters lipid emulsification and lipolysis Therefore, the viscosity developed by the guar gum, which increases the gastric emptying and leads to a prolonged absorption in the small intestine, is likely to be to improve the blood lipids profile.

Therefore, the biscuit of the present invention, by combining both a low glycemic index and the development of a high viscosity of the bolus, can also be used to actively lower blood LDL-cholesterol concentration or to maintain normal blood cholesterol concentrations, and thus to prevent the genesis of cardiovascular disease through reduction of LDL-cholesterol and reduction of inflammatory parameters in healthy subjects or subjects at risk of cardiovascular disease.

A further object of the invention is therefore the use of a biscuit according to the present invention to help control the blood glucose level in healthy subjects or in subjects suffering from insulino-resistance or diabetes and especially type-2 diabetes and/or to actively lower blood LDL-cholesterol concentration or to maintain normal blood cholesterol concentrations for healthy subjects or subjects at risk of cardiovascular disease.

In the digestion process, once the oro-pharyngeal cavity gone through, nutrients start filling the stomach. This part of the digestion is crucial for the development of satiation and satiety feelings. Two key parameters have been identified in this process i.e. the gastric emptying (mainly through its speed) and the various chemical reactions that can happen in the stomach.

A delayed gastric emptying may increase or prolong satiety signals arising from the stomach and thus may result in a higher sensation of satiety. It may also lead to a slower nutrients absorption in the small intestine and thus contribute to prolong the secretion of satiating hormones from the small intestine.

A delay in gastric emptying is observed when a high level of viscosity for the bolus is obtained.

Additionally, gastric emptying is also known to be correlated with hunger feelings.

Therefore, the biscuit of the present invention, by providing a high viscosity of the bolus, can be used to delay gastric emptying and thus to increase the satiety feelings, and thus may result in contributing to weight maintenance up to weight loss, especially in obese subjects.

A further object of the invention is the use of a biscuit according to the present invention to delay gastric emptying and/or to increase the feelings of satiety, and/or to decrease the food intake and/or to contribute to weight management.

A further object of the invention is a biscuit comprising a guar gum having a $t_{0.8}$ (hydration time necessary to reach the $V_{0.8}$ viscosity value corresponding to 80% of the plateau viscosity obtained at 25° C.) ranging from 130 minutes to 390 minutes, preferably from 216 to 390 minutes.

Another object of the invention is a biscuit having a $t_{0.8}$ (hydration time necessary to reach the $V_{0.8}$ viscosity value corresponding to 80% of the plateau viscosity obtained at 25° C.) ranging from 61 and 1060 minutes, preferably from 68 to 370 minutes, and more preferably from 80 and 193 minutes Another object of the invention is a biscuit characterized in that it has a glycemic index equal or less than 25 and more preferably equal or less than 20.

Biscuits are usually obtained by mixing all the ingredients to obtain a dough, forming the dough (using different technologies such as sheeting cutting, laminating, rotary-cutting, wire-cutting, and the like) into individual pieces (usually of a few grams) that are baked until a final low residual moisture is reached.

Hence, another object of the invention is a process of manufacturing the above-described biscuit comprising the following steps:

(a) Mixing the constituents of the biscuit preferably
  (i) Mixing the powdery components first;
  (ii) Subsequently adding the liquid components;
  (iii) Optionally, adding the larger solid components, so-called inclusions in biscuit technology, such as oat flakes, fruit drops, cereal crisps;

(b) Optionally leaving the dough rest, (c) Forming the biscuit and oven bake the obtained formed biscuits.

In a preferred embodiment, the process of manufacturing the above-described biscuit can comprises the following steps:

(a) Mixing the constituents of the biscuit in the following order
  (i) Mixing fats, sugars, emulsifiers, flavours and guar particles with a length between 0.25 and 8 mm, a width between 0.18 and 2 mm and an average length to width ratio between 1.8 and 6;
  (ii) Subsequently incorporating while mixing flours, brans, maltodextrins, non-viscous soluble fibers, raising agents, salt, water;
  (iii) Optionally, incorporating the rest of the constituents of the biscuits such as oat flakes, fruit drops, cereal crisps;

(b) Leaving the dough obtained in step a rest from 5 minutes to 1 hour, (c) Forming the biscuit and oven bake the obtained formed biscuits.

In a more preferred embodiment, the mixing of the constituents can be done in a Hobart mixer of 20 kg capacity and equipped with three variable speeds.

After mixing, the dough can be left at rest for 5 minutes to 1 hour in step (b) of the process, for example in a closed container to avoid any drying.

The temperature of dough at the end of mixing is preferably around room temperature plus or minus 5° C.

Forming step (c) can be carried out using a pilot-scale rotary cutting equipment (De Vurslaag for example). The dough can cut in order to obtain pieces of between 5 and 20 g weight.

The baking step can be operated in a specific pilot-scale oven, such as the one described in patent application EP1545221.

The total baking time can for example be around 5 minutes for a 9 g biscuit and 7 minutes and 30 seconds for a 12 g biscuit.

After baking, the biscuits can be cooled for 15 minutes before packaging, for example in propylene films.

The present invention will be illustrated in details in the examples below.

Example 1

A biscuit dough having the following composition was prepared:

| Example 1 | Dough composition (% by weight) |
|---|---|
| Flour | 28.50 |
| Oat flakes | 15.68 |
| Wheat bran | 4.70 |
| Crystal sugar | 10.12 |
| Fats | 5.27 |
| Fruit drops | 7.13 |
| Polydextrose | 5.13 |
| Maltodextrin | 5.13 |
| Baking powders | 1.57 |
| Rice crisps | 2.85 |
| Emulsifiers | 0.57 |
| Salt | 0.11 |
| Aromas | 0.38 |
| Water | 7.55 |
| Guar particulate according to the invention (HIGRAN-G series from Hindustan Gum) | 5.84 |
| TOTAL | 100% |

The biscuit was prepared according to the following process:
(a) Mixing fat, sugar, emulsifiers, aroma and the guar particles of the invention for five minutes in a Hobart mixer of 20 kg capacity,
(b) Subsequently incorporating flour, brans, maltodextrins, non-viscous soluble fibers, raising agents, salt, water during two minutes,
(c) Incorporating macroscopic inclusions such as oat flakes, fruit drops, cereal crisps for three minutes.

After mixing, the dough is left at rest for 15 minutes, in a closed container to avoid any drying. The temperature of dough at the end of mixing is of 27° C. more or less 2° C.

Forming it then carried out using a pilot-scale rotary cutting equipment (De Vurslag). The dough is cut in order to obtain pieces whose weight is about 9 g.

These pieces are then baked in a specific pilot-scale oven described in patent application EP1545221. The oven is divided in six zones and the temperatures are the following:
Top heat: 150° C., 170° C., 190° C., 190° C., 180° C., 160° C.
Bottom heat: 140° C., 150° C. 160° C., 160° C., 160° C., 160° C.

The baking time is of 5 minutes. The residual moisture at the end of the baking is 3.5% measured after 4 hours in an oven at 103° C.

The biscuits are then cooled for 15 minutes on grids before packaging in propylene films 32M B777.

The foods were tested on 12 subjects in portions containing 50 grams of available carbohydrate together with 250 mL of Evian mineral water, as recommended in Brouns et al, publication "Glycaemic index methodology" Nutrition Research Reviews (2005), 18, 145-171

The GI and II of the subjects were measured according to the protocol disclosed in the specifications.

The GI is the Area Under Curve (AUC) of blood glucose of the test food divided by the AUC of blood glucose after ingestion of the glucose solution and multiplied by 100.

All of the test foods were consumed by the fasting subjects in the morning, at approximately the same time as the subjects would normally consume breakfast.

The results showed below correspond to an average GI and II value between the 12 tested subjects.

| | Glycemic Index | Insulinemic Index |
|---|---|---|
| Biscuit composition of the invention (Example 1) | 43 | 41 |

It can be observed from examples 1, 2 and 3 according to the invention, that the higher the amount of guar particulate, the lower the GI and II of the biscuit.

Example 2

Comparative

Three biscuit dough compositions having the following constitution were prepared:

| | Control | Comparative dough composition (% by weight) | Example 2 (according to the invention) (% by weight) |
|---|---|---|---|
| Flour | 35.35 | 30.14 | 30.41 |
| Oat flakes | 13.83 | 16.58 | 16.73 |
| Wheat bran | 4.92 | 4.52 | 4.56 |
| Crystal sugar | 9.68 | 9.79 | 9.88 |
| Rapeseed oil | 4.76 | 4.67 | 4.71 |
| Fruit drops | 7.68 | 7.53 | 7.60 |
| Polydextrose | 4.92 | 4.97 | 5.02 |
| Maltodextrin | 4.92 | 4.97 | 5.02 |
| Baking powders | 1.60 | 1.57 | 1.57 |
| Rice crisps | 3.07 | 3.01 | 3.04 |
| Emulsifiers | 0.61 | 0.60 | 0.61 |
| Salt | 0.12 | 0.11 | 0.11 |
| Aromas | 0.38 | 0.38 | 0.38 |
| Moisture | 8.15 | 8.14 | 7.30 |
| Coarse guar (HIGRAN-C series from Hindustan Gum) | — | 3.01 | — |
| Guar particulate according to the invention (HIGRAN-G series from Hindustan Gum) | — | — | 3.04 |
| TOTAL | 100% | 100% | 100% |

The three biscuits were prepared according to the process described in example 1.

The GI and II of the subjects were measured according to the protocol disclosed in the specifications, and the results are as follow:

| | Glycemic Index | Insulinemic Index |
|---|---|---|
| Reference biscuit having a low GI with no guar | 55 | 62 |
| Comparative biscuit composition with coarse guar(HIGRAN-C series from Hindustan Gum) | 66 | 62 |
| Biscuit composition of the invention (Example 2) comprising guar particulate according to the invention (HIGRAN-G series from Hindustan Gum) | 47 | 47 |

It can be seen that biscuits according to the invention provide a diminution of the GI and II value of a reference biscuit containing no guar (already having a low GI and a low II).

On the contrary, comparative biscuit composition with coarse guar increases the GI and II value compared to the reference biscuit having a low GI and a low II and containing no guar.

The use of guar particulate according to the invention results in a diminution of the GI and II of the biscuit in which it is introduced.

Example 3

Comparative

In order to show the improvement of the introduction of the guar particulate according to the invention on the preparation process of biscuits compared to the introduction of any other form of guar, biscuits containing different amount of guar gums, in different forms (coarse, fine, and the invention), from 0 up to 18%, were prepared using the same order of incorporation of ingredients and dough mixing sequences as example 1 and 2.

The only parameters of adjustment were the quantity of added water and the baking time. For each formulation, the quantity of water added corresponds to the minimum addition of water required to form a plastic dough, that is able to become cohesive when pressure is applied, stick to the mould during the rotation of the rotary moulder and be deposited onto the belt in a single piece at the end of the rotation cycle.

The biscuit dough according to the invention has the following composition:

The maximum amount of guar beyond which it was no longer possible to form biscuits using the rotary moulding technology was determined.

|  | Biscuit with guar particulate according to the invention (HIGRAN-G series from Hindustan Gum) | Biscuit with coarse guar (HIGRAN-C series from Hindustan Gum) | Biscuit with fine guar (HIGRAN-F series from Hindustan Gum) |
|---|---|---|---|
| maximum amount of guar | 18 | 13 | 8 |

It is observed that the guar particulate according to the invention can be introduced in biscuits in an amount much higher than guar flour (fine guar HIGRAN-F series from Hindustan Gum) and coarse guar (HIGRAN-C series from Hindustan Gum).

The amount of water required to form a dough suitable for rotary moulding technology for compositions comprising 6% of guar was also determined:

|  | Dough composition with 6% guar particulate according to the invention (HIGRAN-G series from Hindustan Gum) | Dough composition with 6% coarse guar (HIGRAN-C series from Hindustan Gum) | Dough composition with 6% fine guar (HIGRAN-F series from Hindustan Gum) |
|---|---|---|---|
| Amount of water | 8.8% | 10.4% | 12.9% |

It is observed that the amount of added water required to form a dough suitable for rotary moulding technology) is less important for compositions comprising guar particulate according to the invention (HIGRAN-G series from Hindustan Gum) than the corresponding amount for compositions comprising coarse guar (HIGRAN-C series from Hindustan Gum) and even less than compositions comprising fine guar (HIGRAN-F series from Hindustan Gum).

The addition of a higher amount of water impacts baking parameters. For example, it becomes necessary to increase the baking time in order to obtain a finished product with the very low moisture content required by the long shelf-life of this category of product. However, at high guar concentration, the constraints cannot be balanced: biscuits produced are under-baked (pale, not crispy enough) and too humid (above 4% moisture), even with a significant increase in baking time, up to 30%. Such increase in baking time also requires slowing down the production line accordingly, which lowers the global productivity and has a negative cost impact.

The maximum amount of guar beyond which a low moisture finished product is no longer obtainable was determined.

|  | Dough composition with guar particulate according to the invention (HIGRAN-G series from Hindustan Gum) | Dough composition with coarse guar (HIGRAN-C series from Hindustan Gum) | Dough composition with fine guar (HIGRAN-F series from Hindustan Gum) |
|---|---|---|---|
| Amount of guar | 18 | 13 | 9 |

It is observed that the guar particulate according to the invention, even when introduced in biscuits in a high amount (18%) can provide a low moisture finished product whereas fine guar (HIGRAN-F series from Hindustan Gum) and coarse guar (HIGRAN-C series from Hindustan Gum) have to be introduced in an amount below 9% and 13% respectively.

Biscuits comprising 20% by weight of guar can be prepared if necessary but with important industrial difficulties and very bad outputs.

Example 4

The present example is intended to show the effect of the biscuit according to the invention on the gastric emptying.

Methodology

Gastric emptying rate (GER) has been measured using dedicated stable isotope $^{13}$C-octanoic breath test technology. The $^{13}$C-octanoic breath test was originally developed by Ghoos et al. (1993) and has been validated against the gold standard scintigraphy using a standard test meal.

For measurement of GER, the stable isotope labelled substrate $^{13}$C-octanoic acid is incorporated into a test meal. $^{13}$C-octanoic acid remains bound to the solid phase of the meal in the stomach and leaves the stomach together with the meal. Upon disintegration of the meal in the duodenum, $^{13}$C-octanoic acid is released and rapidly absorbed, transported to the liver and oxidized to $^{13}CO_2$. The rate at which $^{13}CO_2$ appears in exhaled breath is a measure for the rate of gastric emptying. Breath samples allow collecting the exhaled $^{13}CO_2$.

The $^{13}$C-breath content in the samples is determined using isotope ratio mass spectrometry. It is assumed that the human $CO_2$-production to be 300 mmol/m$^2$ body surface area and the body surface area is calculated by the weightheight formula of Haycock et al. Gastric half emptying time is then calculated by non-linear regression as described by Ghoos et al., (1993).

Ghoos Y F, Maes B D, Geypens B J, Mys G, Hiele M L Rutgeerts P J, Vantrappen G. *Measurement of Gastric-Emptying Rate of Solids by Means of A Carbon-Labeled Octanoic-Acid Breath Test. Gastroenterology.* 1993; 104: 1640-1647.

Haycock G B, Schwartz G J, Wisotsky D H. *Geometric Method for Measuring Body-Surface Area—Height-Weight Formula Validated in Infants, Children, and Adults. Journal of Pediatrics.* 1978; 93:62-66.

Clinical Study Design

A clinical study was conducted to evaluate the impact of guar gum added in low fat, low sugar biscuits on the gastric emptying rate. 20 healthy volunteers took part to the controlled, monocentric, double blind, and randomized crossover trial.

For the purpose of this study, biscuits were specifically produced with the stable isotope: the liquid $^{13}$C-octanoic acid was added to the fat during mixing of ingredients to produce labelled biscuits.

On separate test days, the gastric emptying rate of the 3 different biscuits was evaluated using the dedicated breath test technology. After an overnight fast, 70 g of a biscuit labelled with $^{13}$C-octanoic acid was consumed, followed by measurement of post-ingestion breath $^{13}CO_2$-excretion over six hours. Volunteers blew through a straw into a glass tube to provide Breath samples, that were collected every 15 minutes from baseline up to 6 hours (25 times) to frequently measure exhaled $^{13}CO_2$.

Test Products

Biscuit 1: Low fat, low sugar biscuit containing 6% particulate guar gum

Biscuit 2: Low fat, low sugar biscuit containing 13% particulate guar gum

Biscuit 3: Low fat, low sugar biscuit containing 18% particulate guar gum

The three biscuit dough compositions having the following constitution were prepared:

| Ingredients | Biscuit 1 (% by weight of dough) | Biscuit 2 (% by weight of dough) | Biscuit 3 (% by weight of dough) |
|---|---|---|---|
| Flour | 36.97 | 32.58 | 29.07 |
| Oat flakes | 11.25 | 14.48 | 12.92 |
| Wheat bran | 4.02 | 4.03 | 3.60 |
| Crystal sugar | 13.66 | 13.45 | 13.29 |
| Rapeseed oil | 5.46 | 5.07 | 4.80 |
| Polydextrose | 4.82 | 3.10 | 0.92 |
| Maltodextrin | 4.82 | 1.55 | 0 |
| Baking powders | 1.44 | 1.55 | 1.48 |
| Rice crisps | 1.93 | 1.45 | 1.38 |
| Emulsifiers | 0.64 | 0.42 | 0.56 |
| Salt | 0.12 | 0.08 | 0.07 |
| Moisture | 8.84 | 9.93 | 15.87 |
| Guar particulate according to the invention (HIGRAN-G series from Hindustan Gum) | 5.95 | 12.31 | 16.06 |
| TOTAL | 100 | 100 | 100 |

The nutritional composition of these 3 biscuits was as follows:

| Per portion of 70 g | Biscuit 1 | Biscuit 2 | Biscuit 3 |
|---|---|---|---|
| Energy (kcal) | 242 | 237 | 228 |
| Protein (g) | 6 | 6 | 6 |
| Carbohydrates (g) | 41 | 40 | 37 |
| starch (g) | 29 | 28 | 25 |
| total sugars (g) | 12 | 12 | 12 |
| Fat (g) | 6 | 6 | 6 |
| Total fibre (g) | 8 | 13 | 15 |
| guar gum (g) | 4 | 9 | 13 |
| insoluble fibre (g) | 2 | 3 | 4 |
| soluble fibre (g) | 6 | 10 | 12 |
| Sodium (mg) | 208 | 172 | 186 |

Results

The median gastric emptying time (MGHET) was measured for these 3 biscuits:

| Product | Particulate guar gum concentration (%) | Median gastric half emptying time |
|---|---|---|
| Biscuit 1 | 5.95 | 185 minutes |
| Biscuit 2 | 12.52 | 271 minutes |
| Biscuit 3 | 17.46 | 382 minutes |

These results clearly showed a dose-related increase in gastric half emptying time when increasing doses of guar gum were added to a solid meal.

FIG. 1 illustrates the gastric half emptying time in function of guar gum concentration As shown in FIG. 1, a linear correlation was found between dose of particulate guar gum and gastric half emptying time (median values for Biscuits 1, 2, 3).

Figure 2:
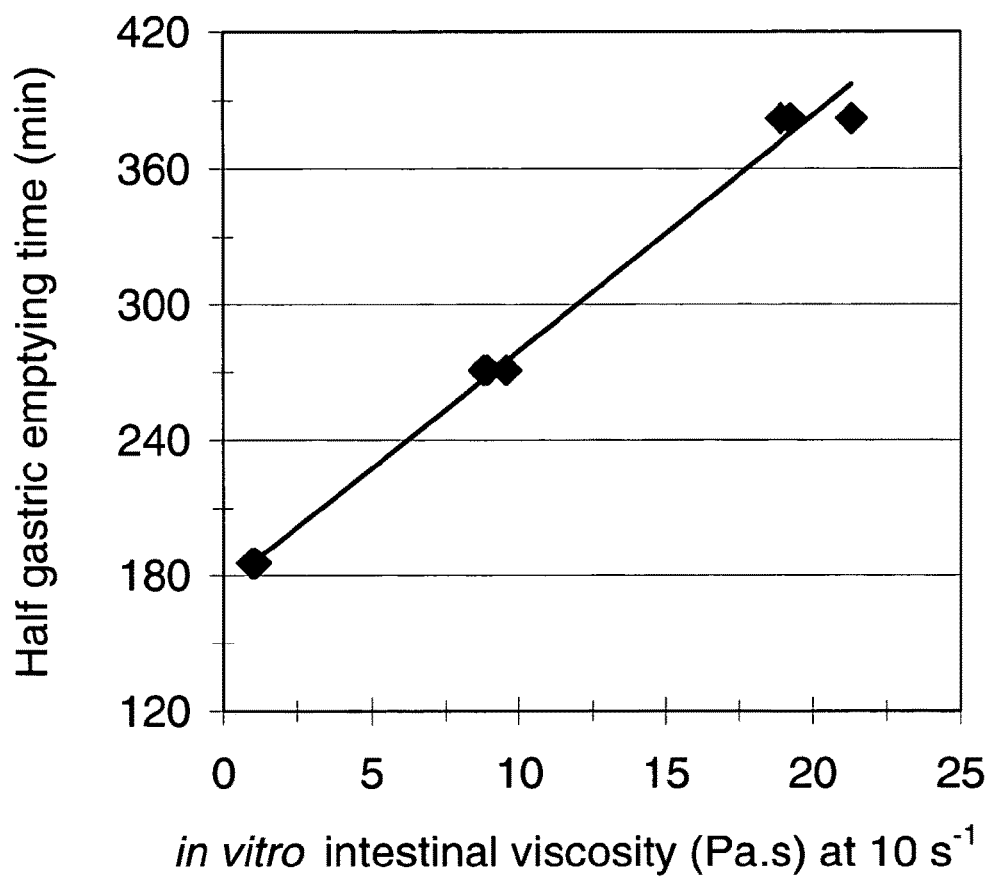
FIG. 2 is a graph showing gastric half emptying time as a function of in vitro intestinal viscosity.

FIG. 2 illustrates the gastric half emptying time in function of in vitro intestinal viscosity. A linear relationship between viscosity and gastric half emptying time was again found in the domain investigated (FIG. 2).

Example 5

The present example is intended to show the results of the biscuits described in Example 4 on GI and II.

GI and II values obtained for biscuits 1, 2, and 3 previously described are as follow

|  | GI | II | Ratio II/IG |
|---|---|---|---|
| Biscuit 1: 6% Particulate Guar Gum | 50 | 49 | 0.98 |
| Biscuit 2: 13% Particulate Guar Gum | 25 | 17 | 0.68 |
| Biscuit 3: 18% Particulate Guar Gum | 17 | 10 | 0.59 |

The biscuits with the highest level of viscosity obtained the smallest GI and II. Increasing the dose of guar gum enrichment in biscuits diminished the GI and II.

The calculated ratio II/IG shows that the biscuits induce the secretion of a small amount of insulin to manage the blood glucose level. A lower absorption of glucose from the intestine involving the digestive tract is observed.

Example 6

The present example is intended to show the effect of the introduction of a specific guar according to the invention on the organoleptic properties of the product.

A sensory test was performed by the external company Adriant according to the guidelines ISO 13299:2003 "Sensory analysis—Methodology—General guidance for establishing a sensory profile". A group of 12 trained experts was asked to compare the sensory attributes of a biscuit containing 13% of guar of the invention with a control biscuit, having a low fiber content. These experts perform weekly sensory evaluation and have been shown to be reproducible and discriminating.

The formula of these 2 biscuits is compared in the following table:

| Ingredients | Dough composition containing guar gum of the invention (% by weight) | Control dough composition (% by weight) |
|---|---|---|
| Flour | 29.01 | 40.41 |
| Oat flakes | 19.51 | 26.81 |
| Wheat bran | 3.90 | 0 |
| Crystal sugar | 11.30 | 11.40 |
| Rapeseed oil | 9.80 | 9.71 |
| Baking powders | 1.10 | 1.30 |
| Aroma | 0.58 | 0.60 |
| Emulsifiers | 0.50 | 0.58 |
| Salt | 0.10 | 0.12 |
| Moisture | 12.40 | 9.07 |
| Guar gum of the invention | 11.80 | 0 |
| TOTAL | 100 | 100 |

Sugar, fat and proteins content were identical and the only difference between these biscuits is the partial replacement of cereals (flour and flakes) by guar gum of the invention. The nutrition composition is the following:

| per 100 g of product | Biscuit containing 13% of guar of the invention | Control biscuit |
|---|---|---|
| Energy (kcal) | 431 | 459 |
| Proteins (g) | 8 | 8 |
| Fat (g) | 15 | 15 |
| Carbohydrates (g) | 57 | 69 |
| Sugars (g) | 15 | 15 |
| Starch (g) | 42 | 54 |
| Fibres (g) | 20 | 5 |
| Guar gum | 13.0 | 0 |

Surprisingly, biscuits containing 13% guar (and 20% fibers in total) were perceived "less hard" than control biscuits containing only 5% of fibers. The mean hardness score was 18.88±7.62 for the biscuit of the invention vs. 22.25±9.66 for the control biscuit. This difference is statistically significant (p=1.3%).

This result is in disagreement with prior art, which consistently showed that addition of even small dosages of guar gum in biscuit lead to significant changes in their texture. Ellis and coworkers (Ellis, P. R., Kamalanathan, T., Dawoud, F. M., Strange, R. N. and Coultate, T. P., *European Journal of Clinical Nutrition*, 1988, 42, 425-435) produced shortbread biscuits containing guar doses between 2% and 6% and evaluated their palatability and physiological effect. The guar used was a high viscosity commercial guar, with a standard granulometry. A significant decrease in palatability is reported by the authors for the biscuits containing 4% and 6% guar gum vs. the control biscuit. A linear relationship was found between guar concentration and hedonic score, indicating that a very low palatability would be expected for a biscuit containing 13% guar gum. It is also important to note that the shortbread biscuits containing a higher level of fat (more than 25% vs. 15% in our case) and sugars (more than 21% vs. 15% in our case), which are known by the man of the art as improvers of texture and taste of biscuits.

The invention claimed is:

1. A biscuit comprising:
   6% to 20% by weight guar gum, the guar gum is a native guar gum in a rod-shaped form with a length between 0.25 and 8 mm, a width between 0.18 and 2 mm and an average length to width ratio between 1.8 and 6;
   less than 25% by weight sugar; and
   less than 20% by weight fat.

2. The biscuit according to claim 1, wherein the biscuit comprises between 6% and 15% by weight, relative to the total weight of the biscuit, of guar gum.

3. The biscuit according to claim 1, wherein the rod-shaped form guar gum has an average length ranging from 1.3 and 4.2 mm.

4. The biscuit according to claim 1, wherein the rod-shaped form guar gum has an average width ranging from 0.6 to 1.3 mm.

5. The biscuit according to claim 1, wherein the rod-shaped form guar gum has an average length to width ratio ranging from 2 and 5.

6. The biscuit according to claim 1, wherein the fat comprises trans fatty acids and saturated fatty acids in an amount respectively below 0.1% and 2% by weight, relative to the total weight of the biscuit.

7. The biscuit according to claim 1, wherein the biscuit comprises 0.2 to 1% by weight of polyunsaturated fatty acids.

8. The biscuit according to claim 1, wherein the biscuit further comprises more than 40% by weight, relative to the total weight of the biscuit, of cereal.

9. The biscuit according to claim 8, wherein the biscuit further comprises more than 40% by weight, relative to the total weight of the biscuit, of whole grains.

10. The biscuit according to claim 1, wherein the guar gum in a rod-shaped form is a high viscosity guar gum having an average molar mass ranging from $1.10^5$ to $3.10^6$ g/mol.

11. The biscuit according to claim 1, wherein the biscuit comprises more than 12% by weight, relative to the total weight of the biscuit, of fibers, with guar gum being comprised in said fibers.

12. The biscuit according to claim 11, wherein the fibers comprise viscous soluble fibers, guar gum being comprised in the viscous soluble fibers, and the fibers optionally further comprise insoluble fibers, and/or non-viscous soluble fibers.

13. The biscuit according to claim 1, wherein the biscuit comprises less than 20% by weight, relative to the total weight of the biscuit, of sugar, less than 10% by weight of fat, more than 40% by weight of cereal, and more than 12% by weight of fibers comprising a mixture of insoluble fibers, viscous soluble fibers and non-viscous soluble fibers.

14. The biscuit according to claim 1, wherein the biscuit further comprises water, in an amount ranging from 0.5 to 5% by weight, relative to the total weight of the biscuit.

15. The biscuit according to claim 1, wherein the biscuit has a water activity (Aw) value between 0.05 and 0.4.

16. The biscuit according to claim 1, wherein the biscuit comprises less than 240 mg of sodium per 100 g of biscuit.

17. A biscuit comprising:
6% to 20% by weight guar gum, the guar gum is a native guar gum in a rod-shaped form with a length between 0.25 and 8 mm, a width between 0.18 and 2 mm and an average length to width ratio between 1.8 and 6;
less than 25% by weight sugar; and
less than 20% by weight fat, relative to the total weight of the biscuit,
wherein the biscuit has a glycemic index equal or less than 55 and/or an insulinemic index equal or less than 60.

18. The biscuit according to claim 1, wherein the biscuit comprises less than 10% by weight, relative to the total weight of the biscuit of fructose and/or less than 10% by weight, relative to the total weight of the biscuit of polyols.

19. A method for controlling blood glucose levels, the method comprising administering the biscuit according to claim 17 to a subject having diabetes or insulino-resistance.

20. A method for decreasing the insulinemic or glycemic index of a biscuit, the method comprising adding guar gum in a rod-shaped form with a length between 0.25 and 8 mm, a width between 0.18 and 2 mm and an average length to width ratio between 1.8 and 6, to a biscuit matrix.

21. The method according to claim 20, wherein the biscuit matrix has an insulinemic index equal or less than 60 and/or a glycemic index equal or less than 55.

22. A method for making a biscuit, the method comprising:
mixing guar gum in rod-shaped form having a length between 0.25 and 8 mm, a width between 0.18 and 2 mm and an average length to width ratio between 1.8 and 6 with flour and liquid;
forming the biscuit; and
baking the formed biscuit,
wherein the biscuit comprises 6% to 20% by weight guar gum, less than 25% by weight sugar, and less than 20% by weight fat, relative to the total weight of the biscuit.

* * * * *